(12) United States Patent
Abboud et al.

(10) Patent No.: US 8,900,222 B2
(45) Date of Patent: Dec. 2, 2014

(54) METHOD AND APPARATUS FOR INFLATING AND DEFLATING BALLOON CATHETERS

(71) Applicant: Medtronic Cryocath LP, Toronto (CA)

(72) Inventors: Marwan Abboud, Pierrefonds (CA); Rachid Mahrouche, Lasalle (CA); Chadi Harmouche, St-Laurent (CA); Teresa Ann Mihalik, Montreal (CA); Giles Desrochers, Beaconsfield (CA)

(73) Assignee: Medtronic Cryocath LP, Toronto, Ontario (CA)

( * ) Notice: Subject to any disclaimer, the term of this patent is extended or adjusted under 35 U.S.C. 154(b) by 0 days.

(21) Appl. No.: 13/749,795

(22) Filed: Jan. 25, 2013

(65) Prior Publication Data
US 2013/0172866 A1 Jul. 4, 2013

Related U.S. Application Data

(60) Division of application No. 11/839,785, filed on Oct. 18, 2007, now Pat. No. 8,382,747, which is a continuation of application No. 11/581,592, filed on Oct. 16, 2006, now Pat. No. 8,491,636, which is a continuation-in-part of application No. 10/806,995, filed on Mar. 23, 2004, now Pat. No. 7,727,228.

(51) Int. Cl.
| | |
|---|---|
| *A61B 18/02* | (2006.01) |
| *A61M 25/10* | (2013.01) |
| *A61B 18/00* | (2006.01) |
| *A61B 18/14* | (2006.01) |
| *A61B 17/22* | (2006.01) |

(52) U.S. Cl.
CPC ............ *A61B 18/02* (2013.01); *A61M 25/1018* (2013.01); *A61B 2018/00994* (2013.01); *A61M 25/1011* (2013.01); *A61B 2018/0212* (2013.01); *A61B 18/1492* (2013.01); *A61B 2018/0022* (2013.01); *A61B 2017/22051* (2013.01); *A61B 2018/0262* (2013.01)
USPC .................. 606/22; 606/20; 606/21; 607/104

(58) Field of Classification Search
USPC ........................ 606/20–26; 607/104–105, 113
See application file for complete search history.

(56) References Cited

U.S. PATENT DOCUMENTS

| | | | |
|---|---|---|---|
| 3,125,096 A | 3/1964 | Antiles et al. | |
| 3,425,417 A | 2/1969 | Kanbar et al. | |

(Continued)

FOREIGN PATENT DOCUMENTS

| | | |
|---|---|---|
| CA | 2547953 A1 | 7/2000 |
| CA | 2 461 217 | 4/2003 |

(Continued)

OTHER PUBLICATIONS

D'Avila, A., et al., Pericardial Anatomy for the Interventional Electrophysiologist, *J Cardiovasc Electrophysiol*, vol. 14, pp. 422-430, Apr. 2003.

(Continued)

*Primary Examiner* — Jaymi Della
(74) *Attorney, Agent, or Firm* — Christopher & Weisberg, P.A.

(57) ABSTRACT

A system and method for controlling the inflation, ablation, and deflation of a balloon catheter. The system includes a balloon catheter, a console, a pressurized gas or liquid inflation source, and an umbilical system to deliver pressurized coolant to the balloon catheter. The system may include controller that monitors the amount of pressure and volume within the balloon catheter. During inflation, the pressure and/or volume of fluid within the balloon is maintained at a target amount in order to provide sufficient mechanized pressure against the desired target region. The system limits the inflation pressure such that a safe quantity of gas would be released should a leak occur. If the amount falls below a certain threshold level, gas or fluid egress is presumed and the inflation process is halted.

11 Claims, 14 Drawing Sheets

(56) References Cited

U.S. PATENT DOCUMENTS

| | | |
|---|---|---|
| 3,903,871 A | 9/1975 | Chisum et al. |
| 3,924,628 A | 12/1975 | Droegemueller et al. |
| 3,938,514 A | 2/1976 | Boucher |
| 4,029,099 A | 6/1977 | Fifield |
| 4,043,341 A | 8/1977 | Tromovitch |
| 4,176,662 A | 12/1979 | Frazer |
| 4,278,090 A * | 7/1981 | van Gerven ............ 606/23 |
| 4,411,656 A | 10/1983 | Cornett, III |
| 4,509,370 A | 4/1985 | Hirschfeld |
| 4,534,339 A | 8/1985 | Collins et al. |
| 4,620,769 A | 11/1986 | Tsuno |
| 4,686,996 A | 8/1987 | Ulbrich |
| 4,704,104 A | 11/1987 | Christensen |
| 4,725,267 A | 2/1988 | Vaillancourt |
| 4,787,882 A | 11/1988 | Clarén |
| 4,813,425 A | 3/1989 | Malis |
| 4,919,112 A | 4/1990 | Siegmund |
| 4,946,440 A | 8/1990 | Hall |
| 5,015,240 A | 5/1991 | Soproni et al. |
| 5,078,713 A | 1/1992 | Varney |
| 5,098,428 A | 3/1992 | Sandlin et al. |
| 5,139,496 A | 8/1992 | Hed |
| 5,151,100 A | 9/1992 | Abele et al. |
| 5,170,787 A | 12/1992 | Lindegren |
| 5,205,298 A | 4/1993 | Hurst |
| 5,217,482 A | 6/1993 | Keith |
| 5,314,408 A | 5/1994 | Salmon et al. |
| 5,324,286 A | 6/1994 | Fowle |
| 5,327,881 A | 7/1994 | Greene |
| 5,334,181 A | 8/1994 | Rubinsky et al. |
| 5,342,298 A | 8/1994 | Michaels et al. |
| 5,363,882 A | 11/1994 | Chikama |
| 5,364,353 A | 11/1994 | Corfitsen et al. |
| 5,409,469 A | 4/1995 | Schaerf |
| 5,423,807 A | 6/1995 | Milder |
| 5,443,470 A | 8/1995 | Stern et al. |
| 5,452,582 A | 9/1995 | Longsworth |
| 5,466,222 A | 11/1995 | Ressemann et al. |
| 5,472,424 A | 12/1995 | Lampropoulos et al. |
| 5,487,385 A | 1/1996 | Avitall |
| 5,496,311 A | 3/1996 | Abele et al. |
| 5,569,161 A | 10/1996 | Ebling et al. |
| 5,575,766 A | 11/1996 | Swartz et al. |
| 5,575,773 A | 11/1996 | Song et al. |
| 5,584,803 A | 12/1996 | Stevens et al. |
| 5,658,278 A | 8/1997 | Imran et al. |
| 5,669,870 A | 9/1997 | Elist |
| 5,673,695 A | 10/1997 | McGee et al. |
| 5,674,218 A | 10/1997 | Rubinsky et al. |
| 5,682,906 A | 11/1997 | Sterman et al. |
| 5,685,878 A | 11/1997 | Falwell et al. |
| 5,697,927 A | 12/1997 | Imran et al. |
| 5,702,368 A | 12/1997 | Stevens et al. |
| 5,713,951 A | 2/1998 | Garrison et al. |
| 5,715,817 A | 2/1998 | Stevens-Wright et al. |
| 5,718,725 A | 2/1998 | Sterman et al. |
| 5,728,151 A | 3/1998 | Garrison et al. |
| 5,735,290 A | 4/1998 | Sterman et al. |
| 5,755,682 A | 5/1998 | Knudson et al. |
| 5,766,151 A | 6/1998 | Valley et al. |
| 5,769,702 A | 6/1998 | Hanson |
| 5,769,812 A | 6/1998 | Stevens et al. |
| 5,792,094 A | 8/1998 | Stevens et al. |
| 5,795,325 A | 8/1998 | Valley et al. |
| 5,814,016 A | 9/1998 | Valley et al. |
| 5,814,097 A | 9/1998 | Sterman et al. |
| 5,827,237 A | 10/1998 | Macoviak et al. |
| 5,833,671 A | 11/1998 | Macoviak et al. |
| 5,855,210 A | 1/1999 | Sterman et al. |
| 5,860,953 A | 1/1999 | Snoke et al. |
| 5,860,970 A | 1/1999 | Goddard et al. |
| 5,860,971 A | 1/1999 | Clarke |
| 5,868,702 A | 2/1999 | Stevens et al. |
| 5,868,735 A | 2/1999 | Lafontaine |
| 5,876,324 A | 3/1999 | Trouchine |
| 5,879,499 A | 3/1999 | Corvi |
| 5,885,238 A | 3/1999 | Stevens et al. |
| 5,885,244 A | 3/1999 | Leone et al. |
| 5,902,299 A | 5/1999 | Jayaraman |
| 5,904,147 A | 5/1999 | Conlan et al. |
| 5,906,579 A | 5/1999 | Vander Salm et al. |
| 5,916,212 A | 6/1999 | Baust et al. |
| 5,938,660 A | 8/1999 | Swartz et al. |
| 5,944,019 A | 8/1999 | Knudson et al. |
| 5,957,963 A | 9/1999 | Dobak, III |
| 5,961,481 A | 10/1999 | Sterman et al. |
| 5,964,778 A | 10/1999 | Fugoso et al. |
| 5,972,013 A | 10/1999 | Schmidt |
| 5,980,486 A | 11/1999 | Enger |
| 6,001,117 A | 12/1999 | Huxel et al. |
| 6,007,571 A | 12/1999 | Neilson et al. |
| 6,012,457 A | 1/2000 | Lesh |
| 6,024,740 A | 2/2000 | Lesh et al. |
| 6,027,476 A | 2/2000 | Sterman et al. |
| 6,033,426 A | 3/2000 | Kaji |
| 6,036,697 A | 3/2000 | DiCaprio |
| 6,043,273 A | 3/2000 | Duhaylongsod |
| 6,059,757 A | 5/2000 | Macoviak et al. |
| 6,060,454 A | 5/2000 | Duhaylongsod |
| 6,087,394 A | 7/2000 | Duhaylongsod |
| 6,093,166 A | 7/2000 | Knudson et al. |
| 6,096,068 A | 8/2000 | Dobak, III et al. |
| 6,101,412 A | 8/2000 | Duhaylongsod |
| 6,106,518 A | 8/2000 | Wittenberger et al. |
| 6,117,101 A | 9/2000 | Diederich et al. |
| 6,123,682 A | 9/2000 | Knudson et al. |
| 6,127,410 A | 10/2000 | Duhaylongsod |
| 6,141,589 A | 10/2000 | Duhaylongsod |
| 6,149,677 A | 11/2000 | Dobak, III |
| 6,161,543 A | 12/2000 | Cox et al. |
| 6,162,171 A | 12/2000 | Ng et al. |
| 6,164,283 A | 12/2000 | Lesh |
| 6,168,586 B1 | 1/2001 | Hahnen |
| 6,179,810 B1 | 1/2001 | Wantink et al. |
| 6,179,827 B1 | 1/2001 | Davis et al. |
| 6,190,348 B1 | 2/2001 | Tiemann et al. |
| 6,190,353 B1 | 2/2001 | Makower et al. |
| 6,214,002 B1 | 4/2001 | Fleischman et al. |
| 6,221,070 B1 | 4/2001 | Tu et al. |
| 6,224,624 B1 | 5/2001 | Lasheras et al. |
| 6,231,518 B1 | 5/2001 | Grabek et al. |
| 6,233,491 B1 | 5/2001 | Kordis et al. |
| 6,235,019 B1 | 5/2001 | Lehmann et al. |
| 6,237,604 B1 | 5/2001 | Burnside et al. |
| 6,237,605 B1 | 5/2001 | Vaska et al. |
| 6,238,371 B1 | 5/2001 | Himbert et al. |
| 6,238,428 B1 | 5/2001 | Werneth et al. |
| 6,241,722 B1 | 6/2001 | Dobak et al. |
| 6,241,754 B1 | 6/2001 | Swanson et al. |
| 6,245,064 B1 | 6/2001 | Lesh et al. |
| 6,245,095 B1 | 6/2001 | Dobak, III et al. |
| 6,248,089 B1 | 6/2001 | Porat |
| 6,248,096 B1 | 6/2001 | Dwork et al. |
| 6,248,117 B1 | 6/2001 | Blatter |
| 6,251,093 B1 | 6/2001 | Valley et al. |
| 6,251,130 B1 | 6/2001 | Dobak, III et al. |
| 6,254,599 B1 | 7/2001 | Lesh et al. |
| 6,254,626 B1 | 7/2001 | Dobak, III et al. |
| 6,258,087 B1 | 7/2001 | Edwards et al. |
| 6,264,679 B1 | 7/2001 | Keller et al. |
| 6,270,482 B1 | 8/2001 | Rosoff et al. |
| 6,270,488 B1 | 8/2001 | Johnson et al. |
| 6,283,127 B1 | 9/2001 | Sterman et al. |
| 6,283,294 B1 | 9/2001 | Thorball et al. |
| 6,290,696 B1 | 9/2001 | Lafontaine |
| 6,305,378 B1 | 10/2001 | Lesh |
| 6,311,692 B1 | 11/2001 | Vaska et al. |
| 6,311,693 B1 | 11/2001 | Sterman et al. |
| 6,312,452 B1 | 11/2001 | Dobak, III et al. |
| 6,314,962 B1 | 11/2001 | Vaska et al. |
| 6,314,963 B1 | 11/2001 | Vaska et al. |
| 6,315,761 B1 | 11/2001 | Shcherbina et al. |
| 6,319,235 B1 | 11/2001 | Yoshino |
| 6,319,248 B1 | 11/2001 | Nahon |

(56) References Cited

U.S. PATENT DOCUMENTS

| | | |
|---|---|---|
| 6,325,067 B1 | 12/2001 | Sterman et al. |
| 6,325,797 B1 | 12/2001 | Stewart et al. |
| 6,350,248 B1 | 2/2002 | Knudson et al. |
| 6,355,029 B1 | 3/2002 | Joye et al. |
| 6,361,519 B1 | 3/2002 | Kjudson et al. |
| 6,383,151 B1 | 5/2002 | Diederich et al. |
| 6,387,092 B1 | 5/2002 | Burnside et al. |
| 6,414,018 B1 | 7/2002 | Kuhaylongsod |
| 6,416,511 B1 | 7/2002 | Lesh et al. |
| 6,428,534 B1 | 8/2002 | Joye et al. |
| 6,432,102 B2 | 8/2002 | Joye et al. |
| 6,440,126 B1 | 8/2002 | Abboud et al. |
| 6,454,794 B1 | 9/2002 | Knudson et al. |
| 6,468,268 B1 | 10/2002 | Abboud et al. |
| 6,471,694 B1 | 10/2002 | Kudaravalli et al. |
| 6,474,340 B1 | 11/2002 | Vaska et al. |
| 6,484,727 B1 | 11/2002 | Vaska et al. |
| 6,502,576 B1 | 1/2003 | Lesh |
| 6,514,245 B1 | 2/2003 | Williams et al. |
| 6,514,249 B1 | 2/2003 | Maguire et al. |
| 6,517,533 B1 | 2/2003 | Swaminathan |
| 6,517,536 B2 | 2/2003 | Hooven et al. |
| 6,527,768 B2 | 3/2003 | Berube |
| 6,540,740 B2 | 4/2003 | Lehmann et al. |
| 6,546,935 B2 | 4/2003 | Hooven |
| 6,551,274 B2 | 4/2003 | Heiner |
| 6,569,082 B1 | 5/2003 | Chin |
| 6,578,579 B2 | 6/2003 | Burnside et al. |
| 6,592,552 B1 | 7/2003 | Schmidt |
| 6,602,276 B2 | 8/2003 | Dobak, III et al. |
| 6,645,202 B1 | 11/2003 | Pless et al. |
| 6,645,234 B2 | 11/2003 | Evans et al. |
| 6,648,878 B2 | 11/2003 | Lafontaine |
| 6,648,879 B2 | 11/2003 | Joye et al. |
| 6,648,883 B2 | 11/2003 | Francischelli et al. |
| 6,652,515 B1 | 11/2003 | Maguire et al. |
| 6,659,981 B2 | 12/2003 | Stewart et al. |
| 6,666,858 B2 | 12/2003 | Lafontaine |
| 6,685,732 B2 | 2/2004 | Kramer |
| 6,689,128 B2 | 2/2004 | Sliwa, Jr. et al. |
| 6,695,769 B2 | 2/2004 | French et al. |
| 6,701,931 B2 | 3/2004 | Sliwa, Jr. et al. |
| 6,702,811 B2 | 3/2004 | Stewart et al. |
| 6,719,755 B2 | 4/2004 | Sliwa, Jr. et al. |
| 6,740,104 B1 | 5/2004 | Solar et al. |
| 6,989,009 B2 | 1/2006 | Lafontaine |
| 2001/0001830 A1 | 5/2001 | Dobak, III et al. |
| 2001/0001831 A1 | 5/2001 | Dobak, III et al. |
| 2001/0002442 A1 | 5/2001 | Dobak, III et al. |
| 2001/0011184 A1 | 8/2001 | Dobak, III et al. |
| 2001/0011185 A1 | 8/2001 | Dobak, III et al. |
| 2001/0016763 A1 | 8/2001 | Lasheras et al. |
| 2001/0021847 A1 | 9/2001 | Abboud et al. |
| 2001/0021865 A1 | 9/2001 | Dobak, III et al. |
| 2001/0021866 A1 | 9/2001 | Dobak, III et al. |
| 2001/0029394 A1 | 10/2001 | Dobak, III et al. |
| 2001/0041923 A1 | 11/2001 | Dobak, III |
| 2001/0044615 A1 | 11/2001 | Amano et al. |
| 2001/0047138 A1 | 11/2001 | Kokate et al. |
| 2002/0007180 A1 | 1/2002 | Wittenberger et al. |
| 2002/0045893 A1 | 4/2002 | Lane et al. |
| 2002/0045894 A1 | 4/2002 | Joye et al. |
| 2002/0115962 A1 | 8/2002 | Fawcett |
| 2003/0018326 A1 | 1/2003 | Abboud et al. |
| 2003/0036752 A1 | 2/2003 | Joye et al. |
| 2003/0060762 A1* | 3/2003 | Zvuloni et al. ............ 604/113 |
| 2003/0187428 A1 | 10/2003 | Lane et al. |
| 2003/0199861 A1 | 10/2003 | Lafontaine |
| 2004/0034344 A1 | 2/2004 | Ryba |
| 2004/0078033 A1 | 4/2004 | Levin |
| 2005/0038421 A1 | 2/2005 | Joye et al. |
| 2005/0182395 A1 | 8/2005 | Lafontaine |
| 2005/0209587 A1 | 9/2005 | Joye et al. |
| 2005/0215989 A1 | 9/2005 | Abboud et al. |
| 2005/0228368 A1 | 10/2005 | Yon et al. |
| 2005/0261753 A1 | 11/2005 | Littrup et al. |
| 2006/0053165 A1 | 3/2006 | Hume et al. |
| 2007/0032783 A1 | 2/2007 | Abboud et al. |

FOREIGN PATENT DOCUMENTS

| | | |
|---|---|---|
| GB | 2163655 A | 3/1986 |
| JP | 2095364 | 4/1990 |
| JP | 5293077 | 11/1993 |
| WO | WO 98/17187 | 4/1998 |
| WO | WO 99/24095 | 5/1999 |
| WO | 0029060 A2 | 5/2000 |
| WO | 0160441 A1 | 8/2001 |
| WO | 0207628 A3 | 1/2002 |
| WO | WO 02/064194 | 8/2002 |

OTHER PUBLICATIONS

Anonymous Author, Flex 10, *Afx Microwave Beating Heart Ablation System*, Products Page, http://www.afx-inc.com/flex10.htm, visited May 4, 2004.

Saltman, A.E., et al., A Completely Endoscopic Approach to Microwave Ablation for Atrial Fibrillation, *The Heart Surgery Forum*, (#2003-11333; Jan. 13, 2003) 6(3): E38-41.

* cited by examiner

METHOD AND APPARATUS FOR INFLATING AND DEFLATING BALLOON CATHETERS

CROSS-REFERENCE TO RELATED APPLICATION

This application is a divisional of U.S. patent application Ser. No. 11/839,785, filed Oct. 18, 2007, now issued U.S. Pat. No. 8,382,747, issued Feb. 26, 2013, which is a continuation of U.S. patent application Ser. No. 11/581,592, filed Oct. 16, 2006, now issued U.S. Pat. No. 8,491,636, issued Jul. 23, 2013, which is a continuation-in-part of U.S. patent application Ser. No. 10/806,995, filed Mar. 23, 2004, now issued U.S. Pat. No. 7,727,228, issued Jun. 1, 2010, the entirety of all of which are incorporated herein by reference.

STATEMENT REGARDING FEDERALLY SPONSORED RESEARCH OR DEVELOPMENT n/a

FIELD OF THE INVENTION

The present invention relates to a method and system for inflating and deflating balloon catheters and more specifically to a method and system for controlling the inflation and deflation of balloon catheters in order to safely and effectively ablate a tissue region.

BACKGROUND OF THE INVENTION

The use of fluids with low operating temperatures, or cryogens, has begun to be explored in the medical and surgical field. Of particular interest are the potential use of catheter based devices, which employ the flow of cryogenic working fluids therein, to selectively freeze, or "cold-treat", targeted tissues within the body. Catheter based devices are desirable for various medical and surgical applications in that they are relatively non-invasive and allow for precise treatment of localized discrete tissues that are otherwise inaccessible. Catheters may be easily inserted and navigated through the blood vessels and arteries, allowing non-invasive access to areas of the body with relatively little trauma.

Catheter-based ablation systems are well known in the art. A cryogenic device uses the energy transfer derived from thermodynamic changes occurring in the flow of a cryogen therethrough to create a net transfer of heat flow from the target tissue to the device, typically achieved by cooling a portion of the device to very low temperature through conductive and convective heat transfer between the cryogen and target tissue. The quality and magnitude of heat transfer is regulated by the device configuration and control of the cryogen flow regime within the device.

A cryogenic device uses the energy transfer derived from thermodynamic changes occurring in the flow of a refrigerant through the device. This energy transfer is then utilized to create a net transfer of heat flow from the target tissue to the device, typically achieved by cooling a portion of the device to very low temperature through conductive and convective heat transfer between the refrigerant and target tissue. The quality and magnitude of heat transfer is regulated by device configuration and control of the refrigerant flow regime within the device.

Structurally, cooling can be achieved through injection of high pressure refrigerant through an orifice. Upon injection from the orifice, the refrigerant undergoes two primary thermodynamic changes: (i) expanding to low pressure and temperature through positive Joule-Thomson throttling, and (ii) undergoing a phase change from liquid to vapor, thereby absorbing heat of vaporization. The resultant flow of low temperature refrigerant through the device acts to absorb heat from the target tissue and thereby cool the tissue to the desired temperature.

Once refrigerant is injected through an orifice, it may be expanded inside of a closed expansion chamber, which is positioned proximal to the target tissue. Devices with an expandable membrane, such as a balloon, are employed as expansion chambers. In such a device, refrigerant is supplied through a catheter tube into an expandable balloon coupled to such catheter, wherein the refrigerant acts to both: (i) expand the balloon near the target tissue for the purpose of positioning the balloon, and (ii) cool the target tissue proximal to the balloon to cold-treat adjacent tissue.

One of the principal drawbacks to such a technique is that during the inflation phase coolant may seep out of the balloon and get into the bloodstream to cause significant harm. Therefore, if the balloon develops a crack, leak, rupture, or other critical structural integrity failure, coolant may quickly flow out of the catheter. Another situation that may occur during the balloon deflation phase is that the balloon may adhere to the ablated tissue causing severe damage. This may occur after cryoablation or cryomapping. Cryomapping is a procedure that chills conducting target tissue to create a transient electrical effect. By temporarily chilling the target tissue, it allows for precise site confirmation in order to prevent inadvertent ablation. During cryomapping, a procedure known as cryoadhesion takes place. Cryoadhesion is a procedure that ensures the catheter tip remains at the target cite for a seamless transition to cryoablation. In a cryoadhesion procedure, the tip of the catheter firmly attaches to the tissue when it freezes thereby reducing the risk of accidental slippage of the catheter tip. Therefore, during unmonitored balloon deflation, i.e. if the balloon deflates too quickly, the balloon, adhering to the tissue walls, may cause severe damage.

Accordingly, it would be desirable to provide an apparatus and method of monitoring and controlling the inflation and deflation phases of a balloon catheter that is adaptable and compatible with all types of balloon ablation catheters, and with all types of ablation procedures, for example RF ablation or cryoablation.

SUMMARY OF THE INVENTION

The present invention advantageously provides a method and system for controllably inflating and deflating a balloon catheter. The method and system allows for the monitoring of the inflation and deflation phases of a catheter system in order to allow ablation to take place, while detecting unwanted leaks of refrigerant into the bloodstream. Balloon leaks are identified, safety evacuation routes are provided, and a controlled deflation mechanism is presented that prevents damage to the interior blood vessel and tissue region, which may occur during unmonitored deflation due to the adherence of the expandable membrane to the interior of the vessel.

In its preferred embodiment, a method of inflating and deflating a catheter during an ablation process, the catheter having an expandable membrane, is provided. The method comprises the steps of controllably inflating the expandable membrane to a target pressure or volume, ablating a desired tissue region while maintaining the target pressure or volume of the expandable membrane, and controllably deflating the expandable membrane so as not to damage desired tissue region.

In another aspect of the invention, a method for inflating and deflating a catheter having an expandable membrane during an ablation process is provided. The catheter is part of a catheter system including a console, the catheter, and an umbilical system coupling the console to the catheter. The method comprises the steps of evacuating air from the expandable membrane by creating a vacuum in the expandable membrane, controllably inflating the expandable membrane proximate a desired tissue region, wherein the expandable membrane is inflated to a target pressure or volume in order to provide sufficient mechanical force against the desired tissue region, ablating the desired tissue region while maintaining the expandable membrane at the target pressure or volume, and controllably deflating the expandable membrane such that the desired tissue region is not damaged.

In still another aspect of the invention, an apparatus for inflating and deflating a catheter having an expandable membrane is provided. The apparatus comprises a console, the console including means for controlling the inflation and deflation of the expandable membrane and for determining if the expandable membrane maintains a target pressure or volume. The console also includes a pressurized inflation source. The apparatus further includes a catheter, and an umbilical system coupling the console to the expandable membrane and delivering pressurized media to the expandable membrane.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

The present invention is an apparatus and method for controlling the inflation and deflation of balloon catheters. In its preferred embodiment, the invention requires four steps to properly control the inflation and deflation of the balloon catheter. However, the invention allows for a variety of different implementations in order to accomplish this task. An intermediary control station containing a shut off valve and/or a coolant source may be implemented to assist in properly monitoring, controlling and maintaining the target balloon pressure and/or volume.

Figure 1A:
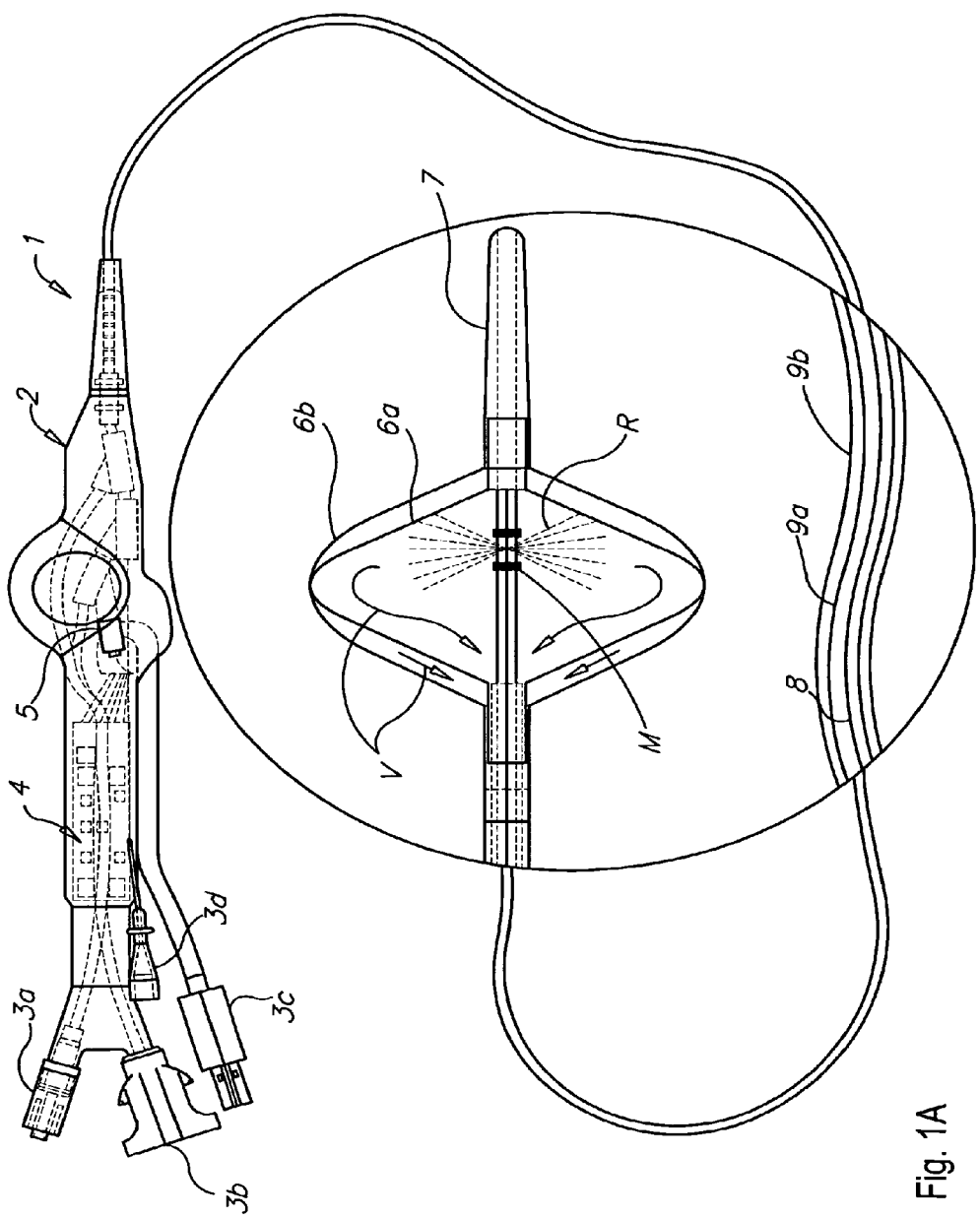
FIG. 1A illustrates a first embodiment of a double balloon catheter used in conjunction with the present invention.

Referring now to the drawing figures in which like reference designations refer to like elements, a first embodiment of a double balloon catheter used in conjunction with the present invention is shown in FIG. 1A. The catheter 1 includes a handle 2 having a number of proximal connector ports 3a-3d. Port 3a may be a first vacuum connector, having a first vacuum lumen therein, such as a 10 French lumen. Port 3b may be a coaxial connector having both a vacuum lumen and injection therein, the vacuum lumen being a second vacuum lumen, such as a 8 French lumen. Port 3c may be an electrical connector. Port 3d may be a guidewire luer hub.

The handle 2 further includes a blood detection board 4 and pressure relief valve 5. The distal end portion of the catheter 1 includes two balloons: an inner balloon 6a and an outer balloon 6b surrounding inner balloon 6a. A soft distal tip 7 is located just distal to the two balloons 6a and 6b. When refrigerant is injected into the balloons along lines R as shown, vacuum applied through the ports 3a and 3b will serve to draw any fluid within balloons 6a and 6b along arrows V out of the balloons and the catheter. Radiopaque marker bands M are located proximate the exit point of the refrigerant injected into balloon 6a to aid in the positioning and tracking of the device.

Catheter 1 includes an elongate shaft having a guidewire 8 and an inner shaft 9a and outer shaft 9b. Exemplary embodiments of the inner shaft 9a include an 8 French shaft, while exemplary embodiments of the outer shaft 9b include a 10 French shaft.

Figure 1B:
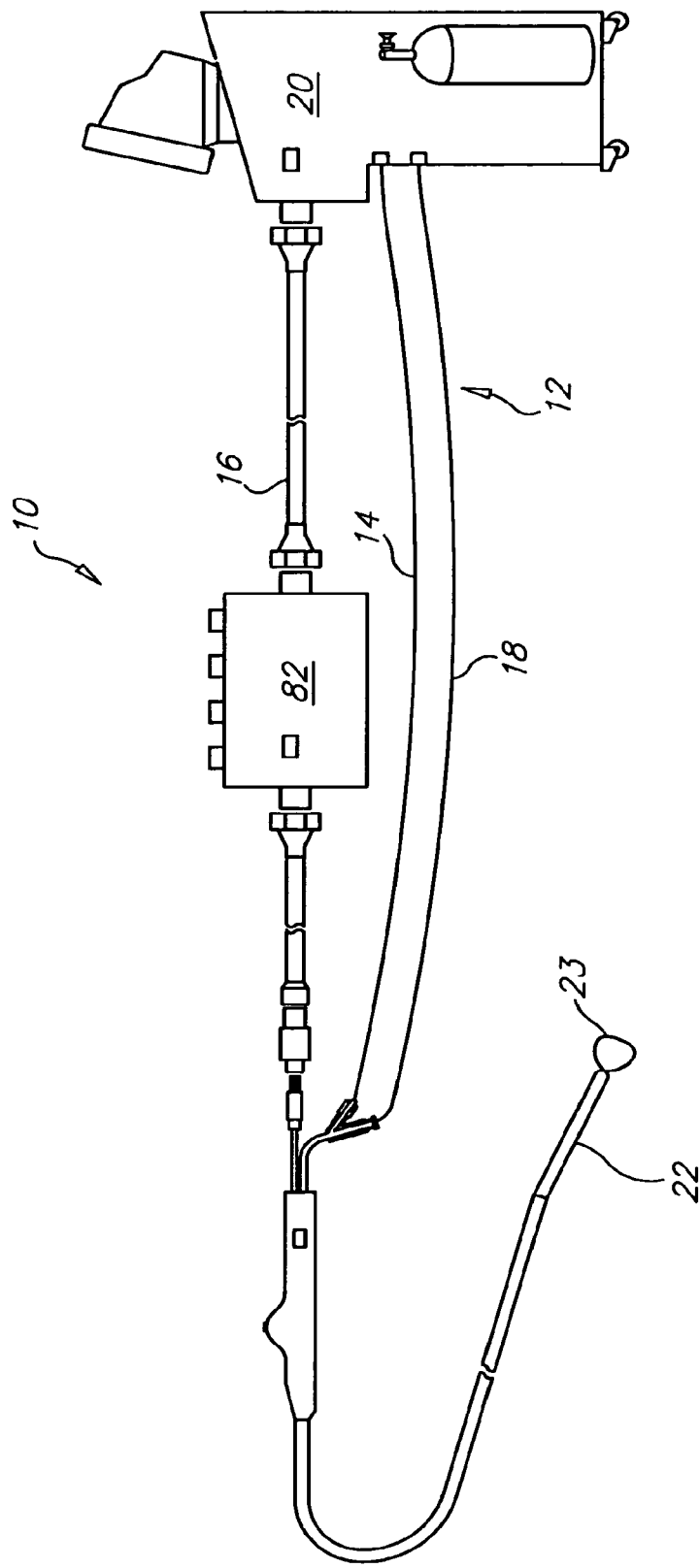
FIG. 1B illustrates a catheter system used in conjunction with the present invention.

A typical catheter system 10 is shown in FIG. 1B. The system includes a console 20 coupled to one end of an umbilical system 12. The opposing end of umbilical system 12 is coupled to an energy treatment device 22. Energy treatment device 22 may be a medical probe, a catheter, a balloon-catheter, as well as other devices commonly known in the art that are smooth enough to pass easily through blood vessels and heart valves. As shown in FIG. 1A, the energy treatment device 22 includes a balloon structure 23 that can be a single wall or a double wall configuration, wherein the double wall configuration places the space between balloon walls in communication with a vacuum source.

Umbilical system 12 is comprised of three separate umbilicals: a coaxial cable umbilical 14, an electrical umbilical 16 and a vacuum umbilical 18. An outer vacuum umbilical is used in the case of a double balloon system; it is not necessary for a single balloon system having only one vacuum lumen. If the user wishes to perform an RF ablation procedure, radiofrequency energy can be provided to electrodes on device 22 via electrical umbilical 16 to perform an RF ablation technique as is common in the art. Electrical umbilical 16 can include an ECG box 82 to facilitate a connection from electrodes on catheter 22 (not shown) to an ECG monitor. Coaxial umbilical 14 includes both a cooling injection umbilical and a vacuum umbilical that provide respective inlet and return paths for a refrigerant or coolant used to cool a tissue-treating end of device 22. The vacuum umbilical 18 is used as safety conduit to allow excess coolant or gas to escape from device 22 if the pressure within the balloon on device 22 exceeds a predefined limit. The vacuum umbilical 18 can also be used to capture air through a leak of the outer vacuum system where it is outside the patient and as a lumen to ingress blood when in the patient.

Referring once again to FIG. 1B, catheter system 10 may include one or more sensors #, which are used to monitor the amount of fluid or gas refrigerant injected through the umbilical system and into the balloons. It is contemplated that the sensors may be located in one of several locations throughout catheter system 10. For example, sensor 11 may be located in console 20, ECG Box 82, and/or handle 2.

Figure 1C:
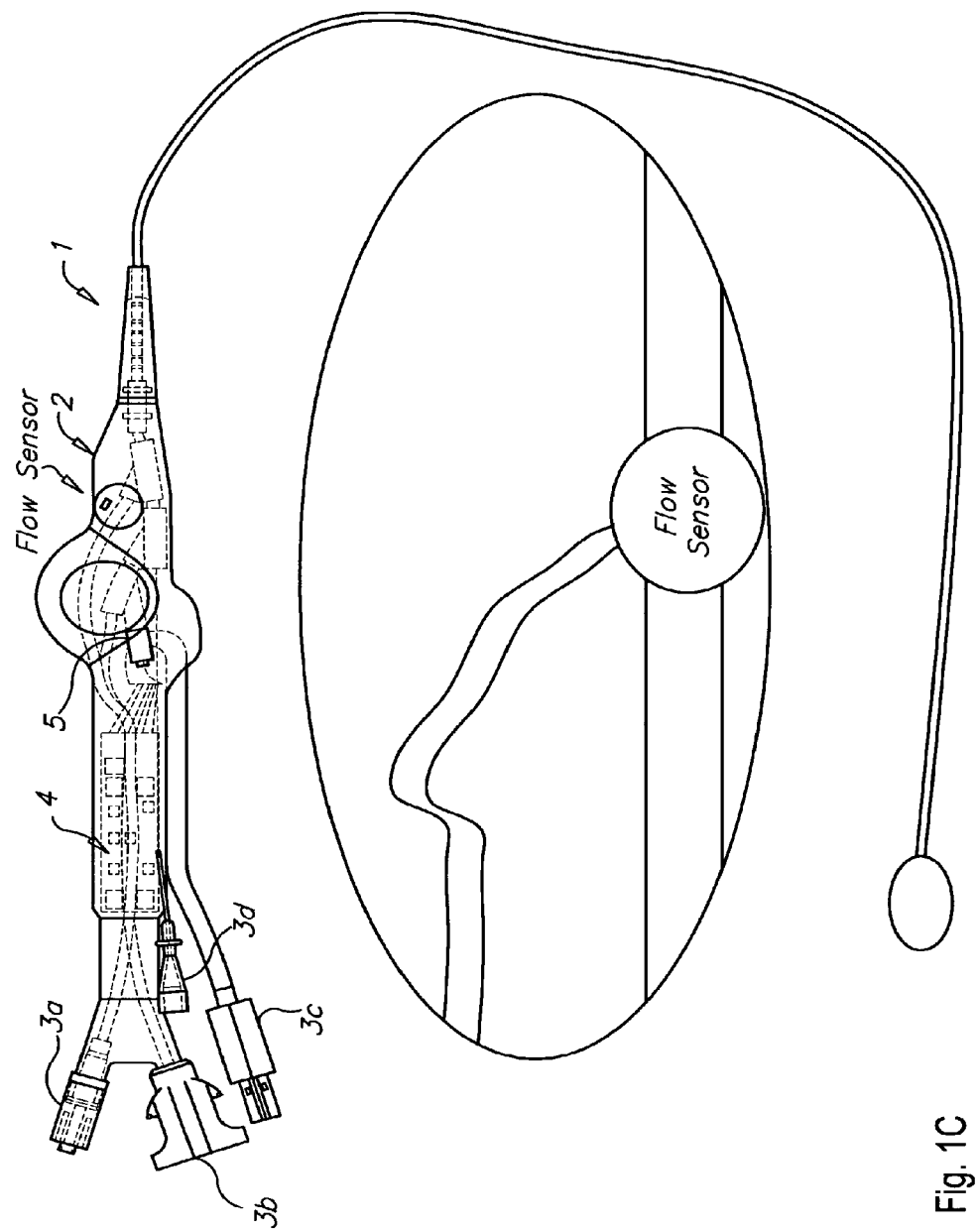
FIG. 1C illustrates the double balloon catheter of FIG. 1A including a flow sensor located in the handle of the catheter.

Two different types of sensors are contemplated for use with the present invention in order to monitor how much coolant is flowing into the balloons. A flow sensor 13 shown in FIG. 1C, measures the rate or speed of fluid or gas at a certain location. An exemplary embodiment of flow sensor 13 is the Microbridge Mass Air Flow Sensor by Honeywell®.

Figure 1D:
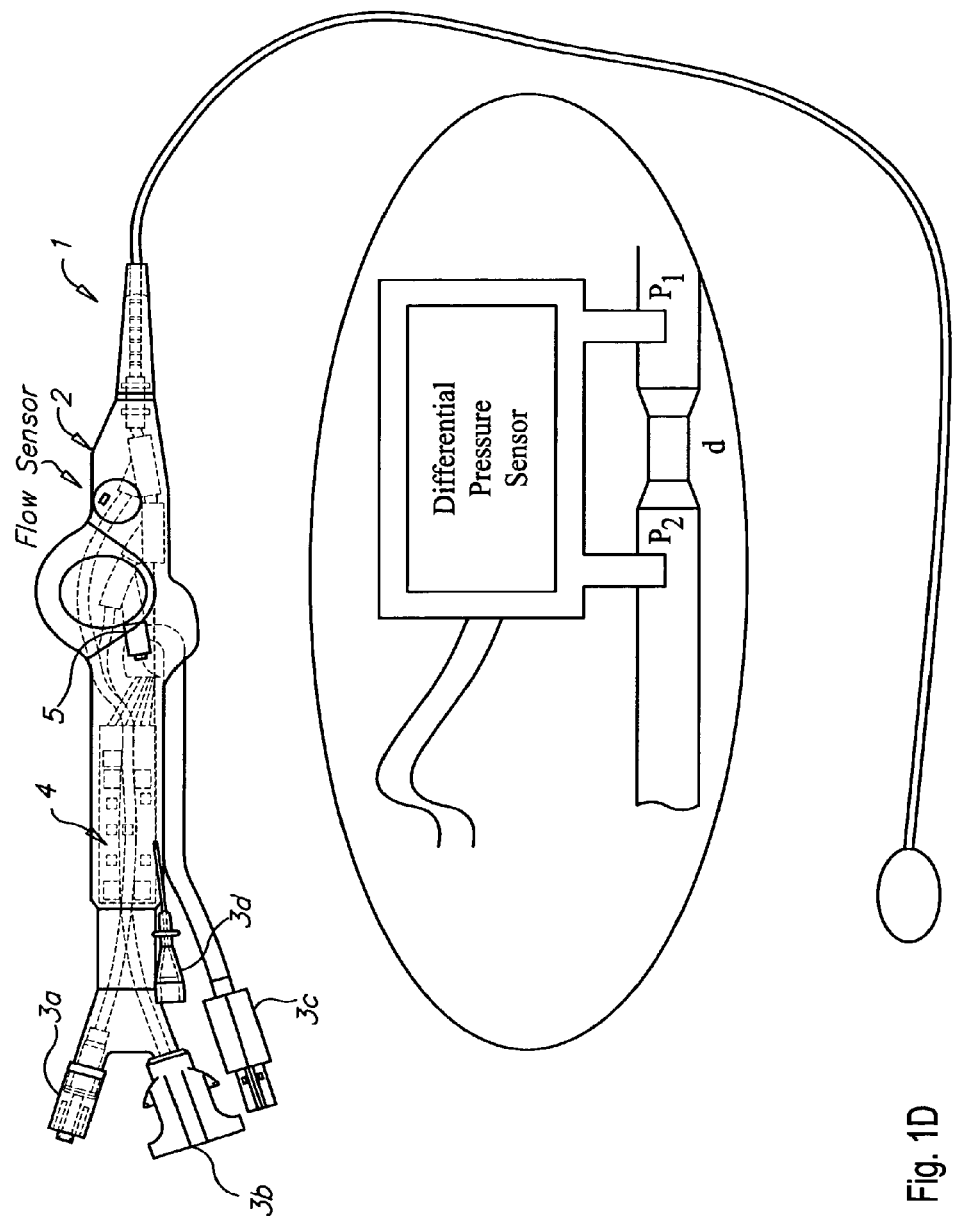
FIG. 1D illustrates the double balloon catheter of FIG. 1A including a pressure sensor located in the handle of the catheter.

Alternately, one or more sensors 11 may be a pressure sensor 15 as shown in FIG. 1D. Pressure sensor 15 in FIG. 1D is a differential pressure sensor that can determine the amount of pressure in the balloons by determining the difference in pressure between points $p_1$ and $p_2$ and the velocity through the restriction point d. An exemplary embodiment of pressure sensor 15 is the 26PC SMT Pressure Sensor by Honeywell®.

FIGS. 2A-2E illustrate different embodiments of the catheter system 10 of the present invention. In general, the inflation/deflation system described herein can be used with both single and double balloon systems. For a single balloon system, the refrigerant is sprayed into the balloon and creates a circumferential region of cooling around the balloon's perimeter. The refrigerant expands and the vapor is drawn back into the console via the return vacuum lumen. With respect to a double balloon system, a second balloon and second vacuum lumen envelop the single balloon system and are always maintained under vacuum for safety reasons. The vacuum of the outer balloon will capture refrigerant escaping through any breach of the inner balloon system. A flow switch mounted on the outer vacuum system is used to monitor any flow activity. Under normal operation, no fluid should pass through the outer vacuum system. Any discussion of a "flow switch" herein implies a double balloon system. Otherwise, all inflation/deflation methods also apply to a single balloon catheter.

Each embodiment includes a console 20 or console 21, an umbilical system comprised of varying combinations of separate umbilicals, and an ablation device 22. Each of the embodiments shown in FIGS. 2A-2E is represented by more detailed corresponding schematics in FIGS. 7-11, respectively, and are discussed in greater detail below.

Figure 2A:
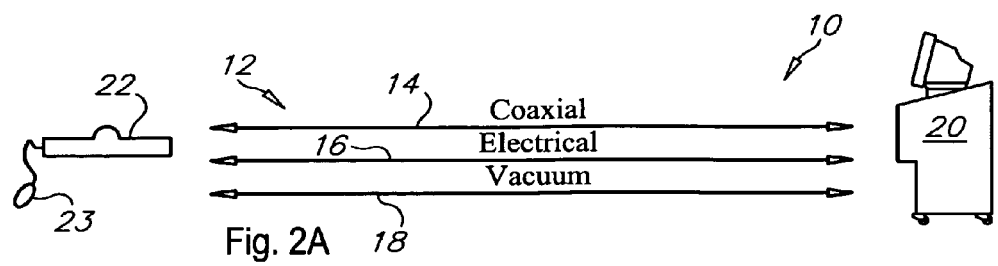
FIGS. 2A-2E illustrate a cryoablation system incorporating various embodiments of the apparatus and method of the present invention.

FIG. 2A represents a typical catheter ablation system 10. Console 20 is coupled to a catheter 22 via an umbilical system 12, comprised of coaxial umbilical 14, which transfers coolant from console 20 to catheter 22 and provides a return conduit for the coolant, electrical umbilical 16, which transfers RF energy from console 20 to catheter 22 during an RF ablation procedure or electrical signals during a cryoablation procedure, and safety vacuum umbilical 18, to allow for quick evacuation of coolant if needed.

Coolant is provided by a coolant source within console 20. Coolant, typically $N_2O$, passes through the internal piping of console 20 before being transferred to catheter 22 via the coaxial umbilical 14. At the distal end of the umbilical, inside catheter 22, the coolant is released inside the catheter tip cavity, which is under vacuum. Both the phase change from liquid to gas and the sudden expansion of the coolant are endothermic reactions, causing a temperature differential which results in the catheter tip or balloon freezing. The coolant vapor is then returned through the vacuum path via umbilical 14 and into console 20, where it is evacuated through a scavenging line.

Figure 2B:
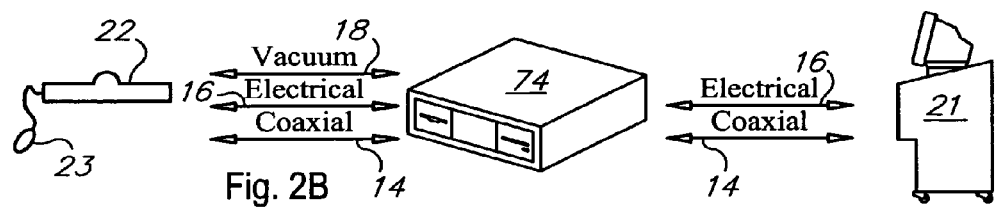

FIG. 2B represents another catheter ablation system. However, in this embodiment, an intermediary station 74 is inserted into the catheter system. As explained in greater detail below, station 74 contains detection valves to detect a drop in balloon pressure which might indicate a leak, and shut off valves to terminate balloon inflation if necessary. Station 74 is coupled to console 21 and catheter 22 via electrical umbilical 16 and coaxial umbilical 14. Vacuum umbilical 18 provides an emergency evacuation path for coolant from the catheter.

Figure 2C:
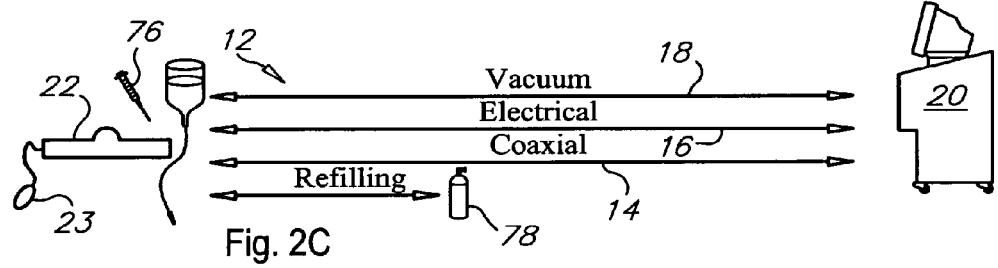

FIG. 2C represents the catheter ablation system of FIG. 2A including a secondary coolant source 78 used to re-inflate the expandable membrane, or balloon 23 of catheter 22 via syringe 76.

Figure 2D:
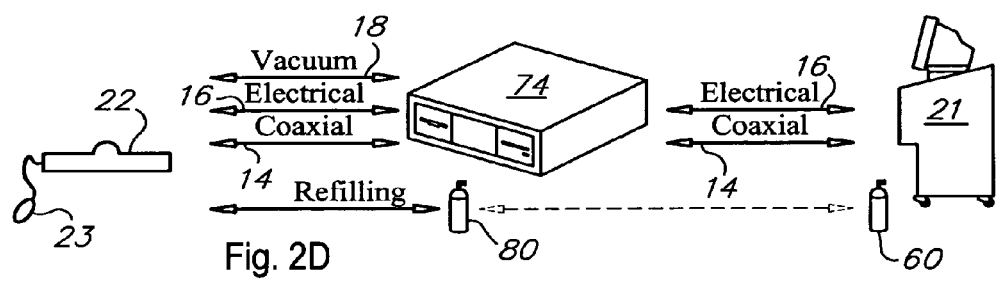

FIG. 2D illustrates two possible configurations for the ablation system. In a first configuration, a secondary coolant source includes a small tank or canister 80 located within an intermediary station 74. In a second configuration, the secondary coolant source includes a small tank or canister 60 located inside the console 21. In both configurations, the secondary coolant source is independent from the source of cooling provided by other components within the console 21 (the primary coolant source), and it does not require the same type of refrigerant that is provided by the primary coolant source.

Figure 2E:
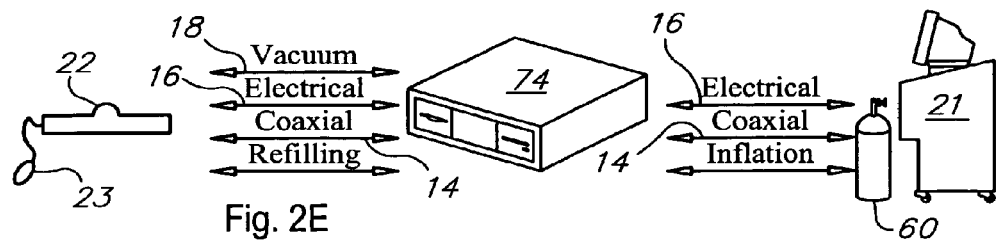

FIG. 2E illustrates a configuration where the secondary cooling source and the primary cooling source are unified and thus share the same source of refrigerant.

Figure 3:
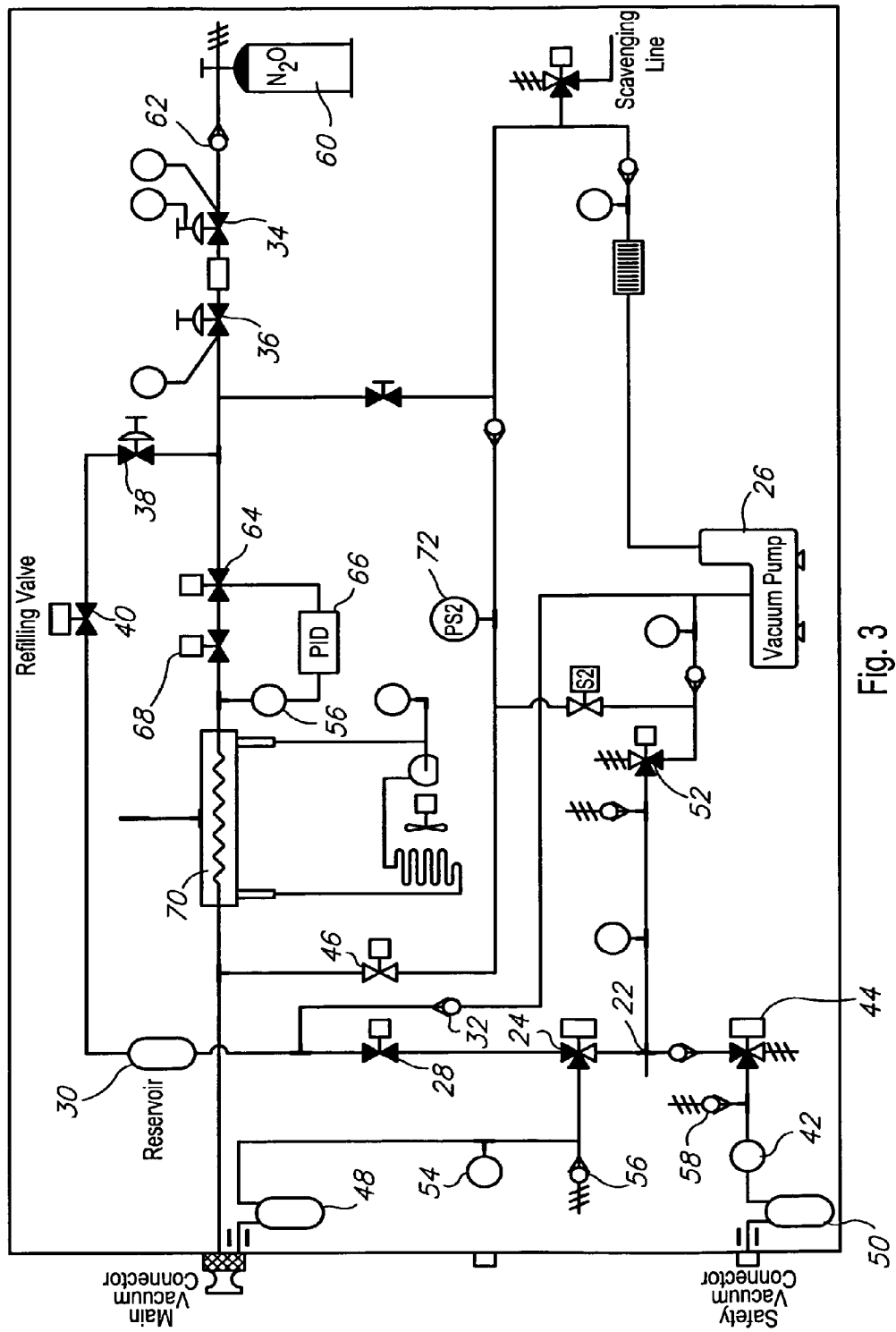
FIG. 3 is a schematic representing the mechanical components of the control console of the present invention.

FIG. 3 refers to a schematic representing the console 20 portrayed in FIGS. 2A and 2C. The schematic shown is designed specially for balloon catheters and contains a series of two and three-way solenoid valves and regulators that assist in monitoring the pressure of the balloon catheter 23, which may drop quickly if a leak of fluid occurs. Device 22 (shown in FIGS. 2A-2E) is a catheter with an expandable membrane 23 at its distal end. Console 20 is represented by the schematic in FIG. 3 that shows the layout of the internal mechanical components of console 20.

In an exemplary embodiment, the system is operated in four phases. The first phase is the evacuation/flushing phase. When the catheter 22 is inserted inside the patient it is first necessary to evacuate air molecules from within the catheter, air contained inside the umbilical connecting the catheter 22 to the console 20, as well as from the catheter shaft itself. Although it is not theoretically possible to evacuate 100% of the air molecules, by minimizing the amount of air within the umbilical and catheter shaft, the catheter is prepared for inflation and then ablation, while minimizing the dangers associated with fluid egress.

During the evacuation/flushing phase, a 3-way solenoid valve 24 is open toward vacuum pump 26, which ensures that there is a vacuum in catheter 22. The 3-way solenoid valve 24 can be replaced by a PID-driven proportional valve. In either configuration, the 2-way solenoid 28 that supports high pressure is closed to prevent any high-pressure gas from reservoir 30 from entering the inner vacuum system/balloon catheter during the refilling process. Reservoir 30 could be a tube or reservoir containing enough fluid volume to fill the umbilical tubes and catheter 22 to a predefined pressure. If the pressure within reservoir 30 exceeds a predetermined pressure setpoint, a check valve 32 will open to evacuate the exceeded amount of coolant such as, for example, nitrous oxide ($N_2O$) in the system in order to keep a fixed amount of nitrous oxide in reservoir 30. During this phase, reservoir 30 is filled with $N_2O$ received from $N_2O$ source 60. The $N_2O$ is received from a high pressure line after leaves tank 60 and passes through a series of regulators, namely, a first regulator 34, a second regulator 36 and then into either a third regulator 38 or a proportional valve, that are adjusted to the predetermined pressure. The reservoir pressure can be controlled through a pressure regulator 38 or through a proportional valve that would refill the tank with different pressure setpoints for different balloon sizes or different inflation pressures. The pressure setpoint can be programmed into a circuit, chip or other memory device that can be located in the handle.

Refilling valve 40 opens for a period of time and fills reservoir 30. During this phase, the 2-way solenoid valve 28 remains closed. Also, during this phase, the system is under vacuum and provides verification for any leaks that occur.

Thus, when the catheter is outside the patient, any breach of the inner or outer vacuum systems will be detected by a high baseline flow through the console flow meter. In addition, a flow switch located in the console or in the catheter handle and mounted on the outer vacuum system will also detect a leak of air through a breach of the outer balloon or vacuum lumen. The flow switch is capable of detecting volumes of gas as little as 1 cc of vapor, and flow rates as little as 20 sccm. When the catheter is inserted into the patient, blood ingress through either the inner or outer vacuum lumens or both will be detected by the leak and blood detection systems. In the case of a constant pressure inflation with circulating flow, the balloon pressure can also be controlled with a PID-driven proportional valve located on the return vacuum lumen or a three-way solenoid valve in series with a pressure switch or pressure transducer.

Figure 4:
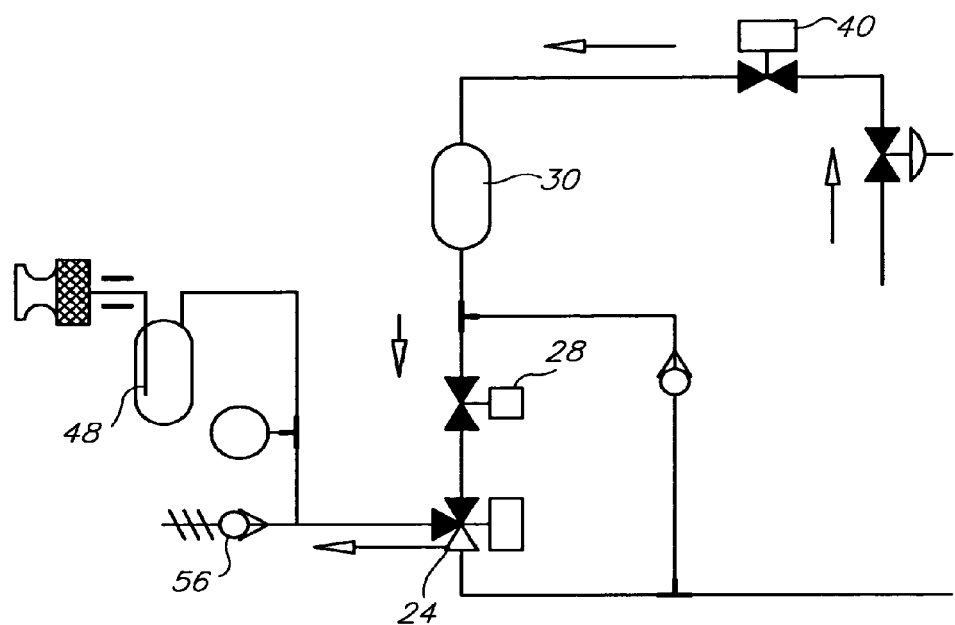
FIG. 4 is a schematic representing the mechanical components of the inflation circuit portion of the control console of the present invention.

Referring to FIG. 4, the inflation phase of the invention will now be discussed. Prior to positioning catheter 22 on the ablation site, the physician must first inflate the expandable membrane 23 inside the heart chamber and then position the balloon 23 proximate the ablation site. During this phase, the system is under vacuum and provides verification for leaks between balloon 23 and the blood. In one embodiment, balloon 23 is inflated by injecting fluid or gas through the umbilical under a fixed flow pressure. This insures a defined and constant pressure inside the balloon in order to provide a mechanical force for inflation. An alternate way to inflate balloon 23 is to use a fixed volume of inflation. This volume would be minimized in order to meet the constraints related to gas egress within the blood stream (maximum of 20 cc within 10 minutes) and meet the requirement for pressure needed to inflate the balloon under the harshest room conditions.

FIG. 3 illustrates the inflation portion of the console mechanics of FIG. 2. During the inflation phase, valve 24 is open toward reservoir 30 and valve 28 opens, while refilling valve 40 remains closed. A fixed amount of $N_2O$ is injected to inflate balloon 23 in order to provide sufficient mechanical force for inflation. If a leak occurs in the balloon, the released volume of $N_2O$ would be no more than 20 cc. The solenoid valve 44 remains open during this phase in order to ensure a vacuum in the safety line. If a leak occurs in the inner balloon of the catheter, the flow switch 42 (FIG. 3), detects leaks as small as 1 cc of vapor. Flow switch 42 is active during all phases to prevent any leak of the inner balloon system in catheter 22. The leak and blood detection systems are still active and monitoring any blood ingress through the outer vacuum lumen. After air has been flushed from catheter 22 and the umbilicals connecting catheter 22 to console 20, and balloon 23 has been inflated, ablation may now take place.

A transition mode follows inflation but precedes ablation. In the case of cryogenic ablation systems, a transition method is needed to transition from closed pressurized volume to an open circuit, which allows the flow of refrigerant to enter and exit the catheter tip while at the same time controlling the balloon pressure in order to keep the balloon inflated and in place. During the transition, a pressure switch, which is adjusted to a pressure higher than atmospheric pressure but preferably lower than 20 psia, monitors the pressure inside the balloon catheter 22. The solenoid valve 24 remains closed until the pressure in the catheter is higher than the preset switch value after which the solenoid valve opens to allow evacuation of excess refrigerant. When the pressure falls below the reset switch value, the solenoid valve 24 closes to keep the balloon inflated and above atmospheric pressure. During the transition, ablation is already initiated but the pressure switch controls the balloon pressure until refrigerant flow alone maintains the balloon open and above atmospheric pressure. The transition phase is considered complete when certain conditions are met: 1) when the pressure switch commands the solenoid valve 24 to open to vacuum and the balloon pressure remains above the present switch value; 2) the duration of the transition phase exceeds a predetermined time; and 3) the injection pressure reaches a predetermined value that is adequate to generate enough flow to maintain the balloon open. Check valve 56 is used to prevent any abnormal rise in the pressure in the catheter tip. Another check valve 58, shown also in FIG. 6, prevents any excessive pressure in the safety vacuum line and in the event the solenoid valve 44 is blocked.

During the ablation phase, refrigerant is injected through the umbilical system into the ablation device 22. When injection of refrigerant is desired, $N_2O$ gas is released from source 60 and provides high pressure liquid through a check valve 62 and a series of pressure regulators 34 and 36. Regulators 34 and 36 are primary and secondary pressure regulators respectively, which serve to bring the gas pressure down to between 810 and approximately 840 psig. The liquid nitrous oxide goes through a proportional valve 64 driven by a Proportional Integral Derivative (PID) controller 66 so that the refrigerant pressure can be varied from 0 psig to approximately 760 psig, and through an injection solenoid valve 68 which remains open. The $N_2O$ then passes through a sub-cooler 70 with various refrigeration components such as a compressor, a condenser, a capillary tube and a heat exchanger, which insures its liquid state through the umbilical and into the small diameter catheter injection tubing. During injection, solenoid vent valve 46 is closed. To detect a failure of this valve, the pressure switch 72 will close when detecting a pressure higher than 15 psig, creating a failure signal.

During the injection phase, proportional valve 64 is used to vary the pressure inside the injection line. This in turn will vary the flow rate of refrigerant to the catheter tip. An increase in the flow rate (less restriction by the regulator) lowers the temperature of the catheter tip. Conversely, decreasing the flow rate allows the catheter tip to be warmed by its surroundings.

Figure 5:
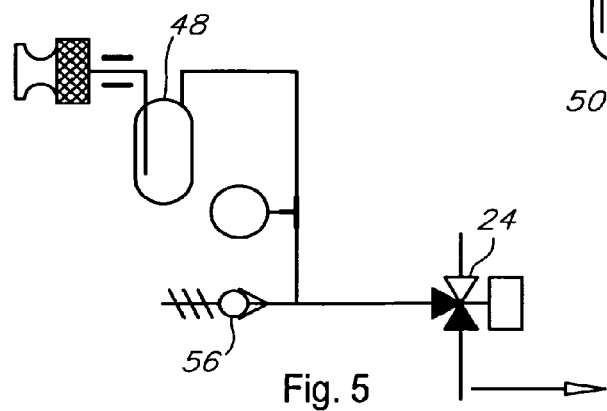
FIG. 5 is a schematic representing the mechanical components of the deflation circuit and main vacuum path of the control console of the present invention.

FIG. 5 illustrates the deflation and main path circuitry of the present invention. At the end of the ablation phase, the system provides a method to insure a controlled/slow deflation in order to prevent damaging the ablated tissue during balloon deflation. This can be a hazard due to cryoadhesion, which may occur when the catheter attaches to the tissue during freezing. Referring to both FIGS. 3 and 5, during deflation, the solenoid valve 24 (FIG. 3) remains closed until the temperature in the balloon is higher than a predetermined temperature (usually above freezing to ensure that surrounding tissue has thawed). When the temperature increases to greater than the predetermined temperature, the solenoid valve 24 opens to vacuum and collapses the balloon. On both vacuum paths, liquid sensors and insulated liquid separators 48 and 50 (FIG. 3) are installed to prevent any liquid from entering the vacuum pump 26. If this occurs, injection and/or inflation will be stopped and both valves 52 (FIG. 3) and 44 (FIG. 3) will switch to atmosphere.

Figure 6:
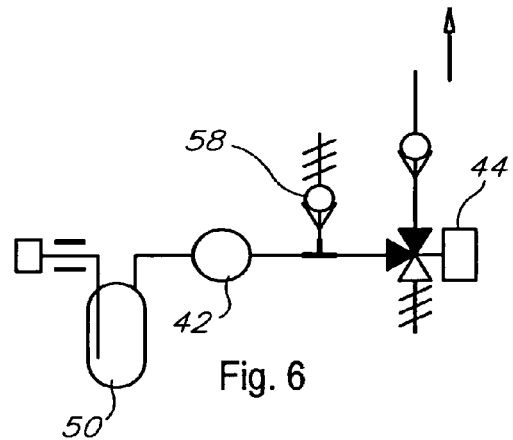
FIG. 6 is a schematic representing the mechanical components of the safety vacuum path of the control console of the present invention.

FIG. 6 illustrates the safety vacuum portion of the console circuitry of FIG. 3. If a leak occurs in the catheter during inflation or ablation, flow switch 42 can detect such a leak in amounts as small as 1 cc of vapor. Upon detection of the leak, inflation of the balloon catheter is stopped. Prior to inflation, the flow switch can detect leaks of the outer balloon or guide wire lumen when the catheter is in the air. In case of pressurization of the safety vacuum line ⅓ psi above atmospheric, a pressure relief valve 58 located distal to the flow switch will vent excess pressure.

Figure 7:
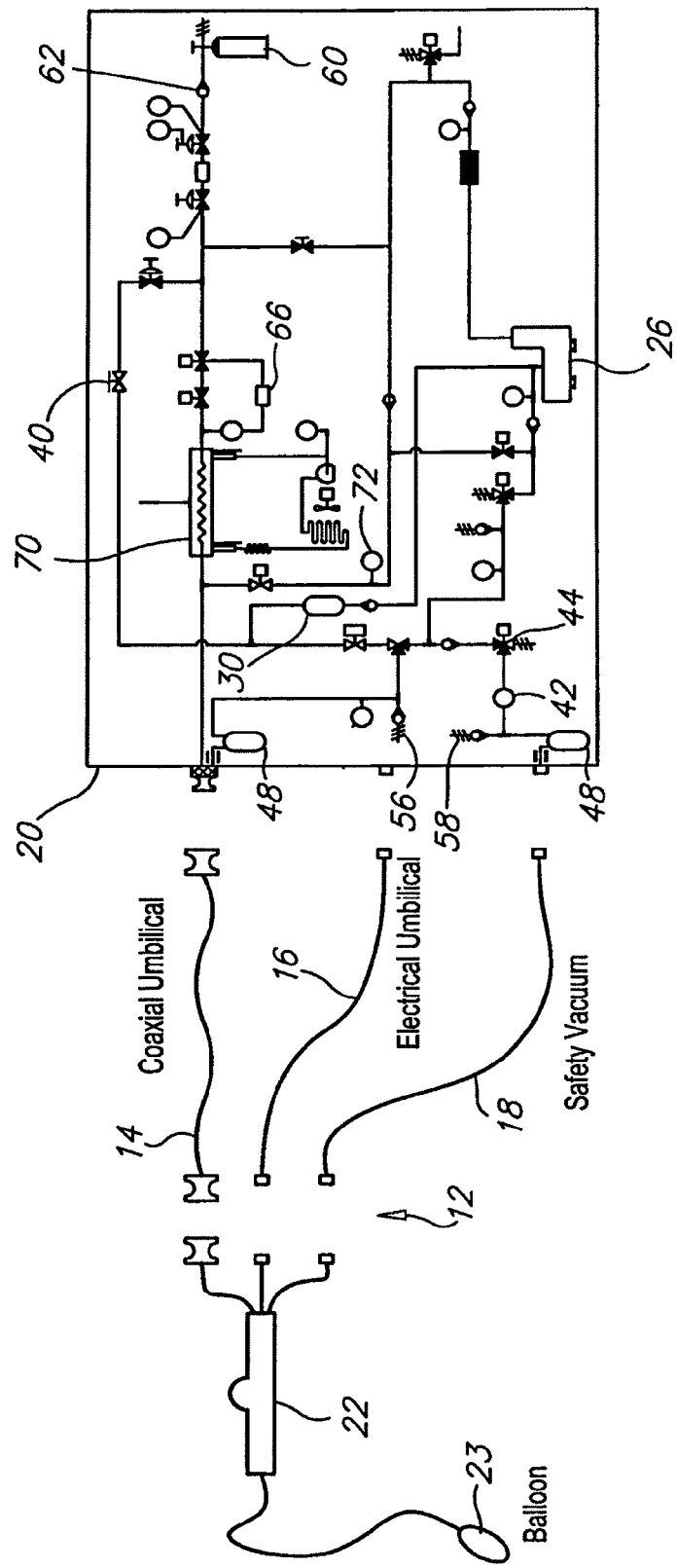
FIG. 7 is a schematic representation of the embodiment illustrated in FIG. 2A.

Referring now to FIG. 7, one embodiment of the present invention is shown. The schematic in FIG. 7 illustrates the mechanical connection of the console 20, umbilical system 12 and catheter 22. The representation in FIG. 7 corresponds to the embodiment shown in FIG. 2A. The internal components of console 20 are similar and correspond to those shown in greater detail in FIG. 3 explained above. In this embodiment, the balloon 23 is inflated by receiving gas or fluid from source 60 via coaxial umbilical 14. PID controller 66 controls the flow of pressurized fluid/gas from console 20 through umbilical system 12 to balloon 23.

Figure 8:
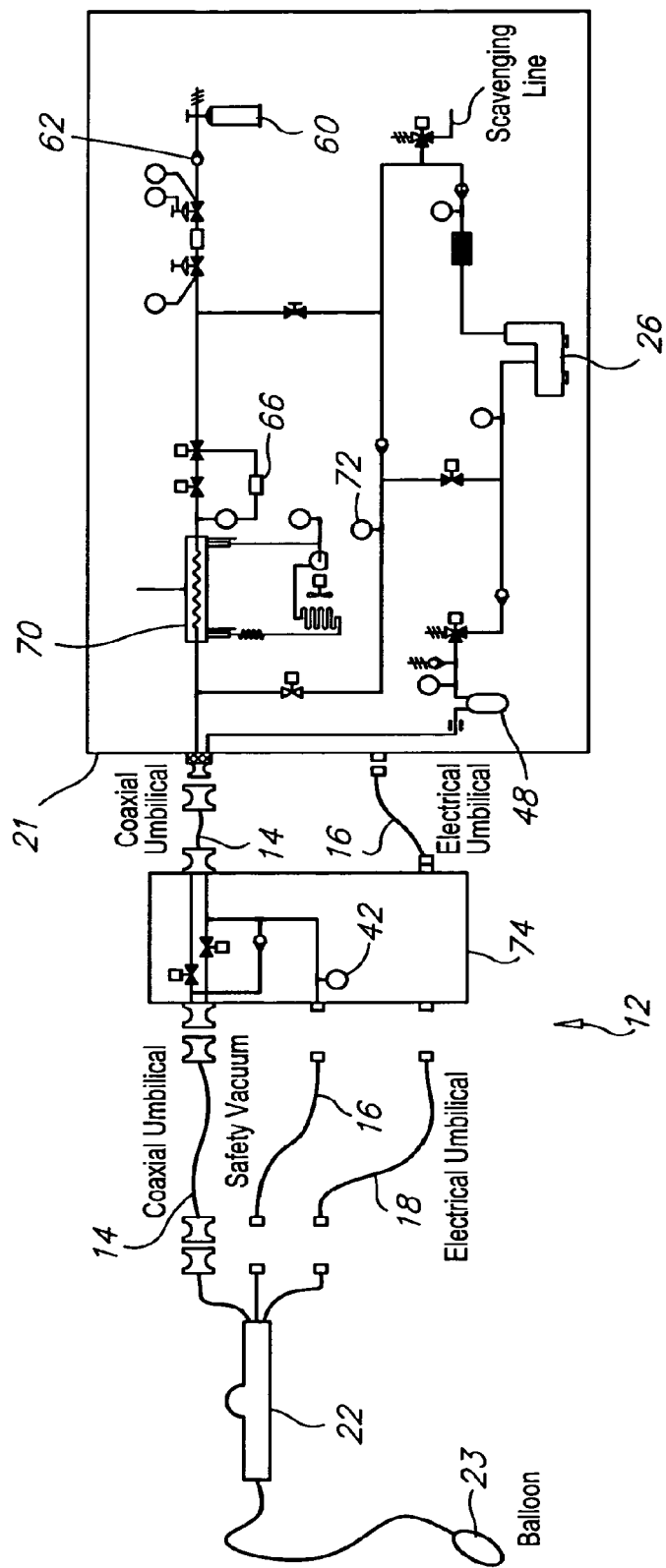
FIG. 8 is a schematic representation of the embodiment illustrated in FIG. 2B.

FIG. 8 shows an alternate embodiment of the invention in which an intermediary station 74 containing all components and circuits to operate the balloon catheter is coupled to console 10, between the console and balloon catheter 23. Station 74 includes a series of shut-off valves and detection switches. Detection circuitry within station 74 can detect if the volume of gas within balloon catheter 23 has exceeded a certain predetermined amount (i.e. 20 cc within the catheter and the umbilical system), and shut-off valves within station 74 are activated, preventing any further inflation. Station 74 advantageously provides a quicker and more effective way of detecting leakage of gas or liquid into the blood stream. If the pressure within balloon catheter 23 drops, this could be an indication that fluid within the balloon has escaped. By inserting station 74 within system 10, a quicker and more efficient way of detecting leaks and preventing unwanted balloon inflation is provided.

Figure 9:
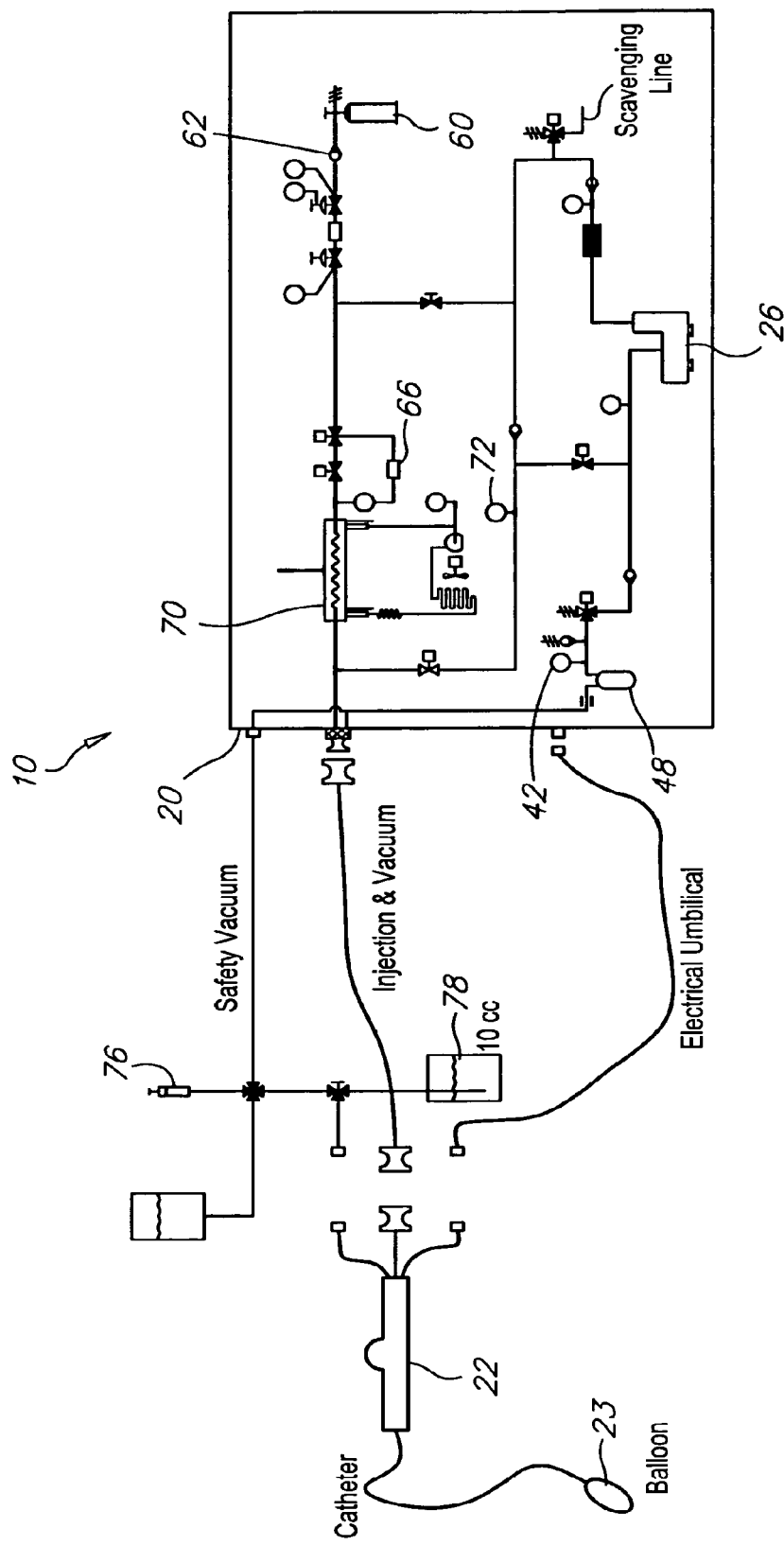
FIG. 9 is a schematic representation of the embodiment illustrated in FIG. 2C.

FIG. 9 shows yet another embodiment of the invention. Here, balloon inflation can be performed by a syringe 76 coupled to a saline water source 78 or any other fluid media including gasses or liquids. This embodiment becomes practical when manual balloon inflation is required.

Figure 10:
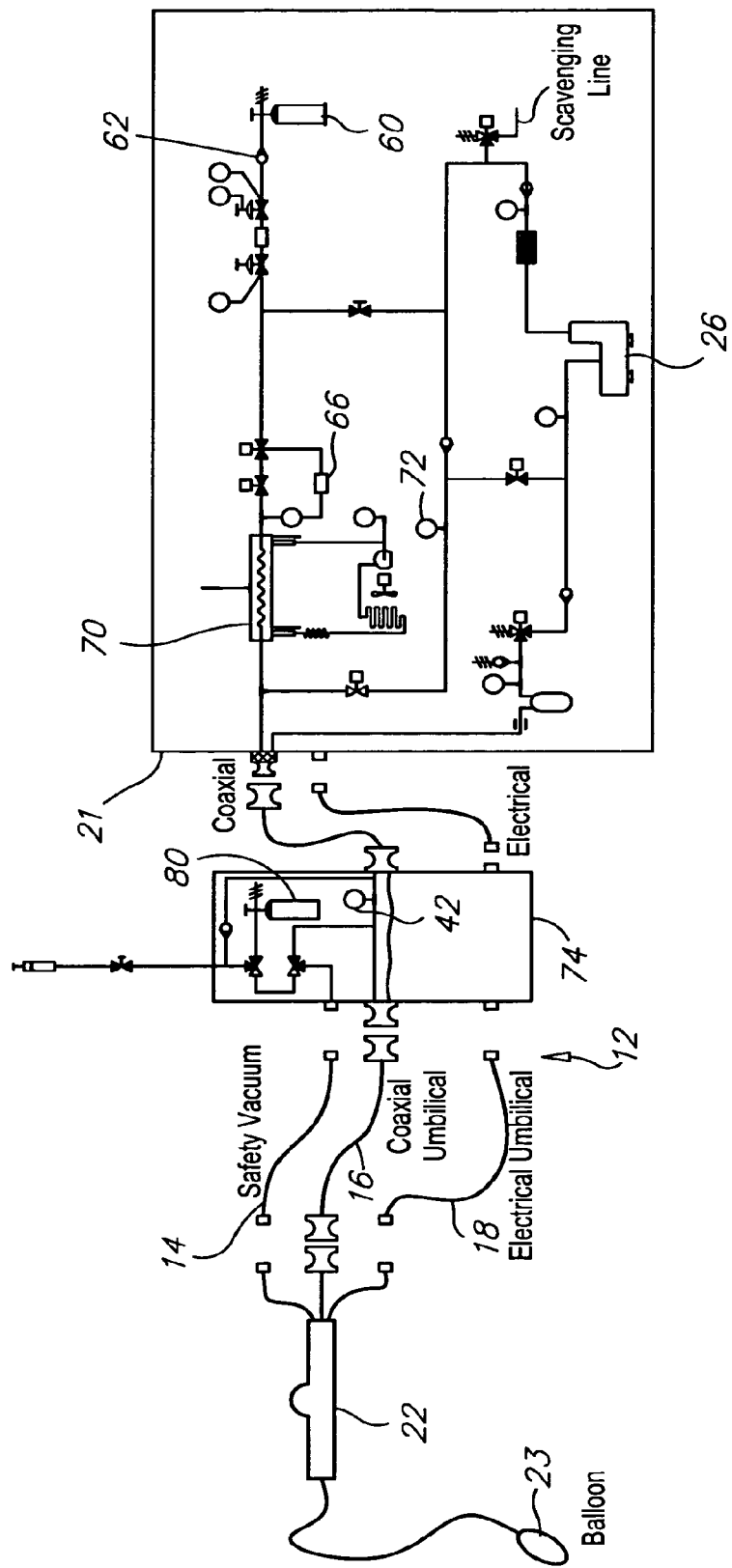
FIG. 10 is a schematic representation of the embodiment illustrated in FIG. 2D.

In FIG. 10, intermediary station 74 includes a second inflation source 80. As in the embodiment depicted in FIG. 8, leak detection circuitry and shut-off valves located in station 74 provide an efficient way of detecting leaks and quickly prohibiting the further inflation of balloon catheter 23. Should further inflation be required, a separate pressurized $N_2O$ source 80 is provided in station 74, which is at a closer and more convenient location, i.e. nearer the catheter and not in a remote location such as console 20.

Figure 11:
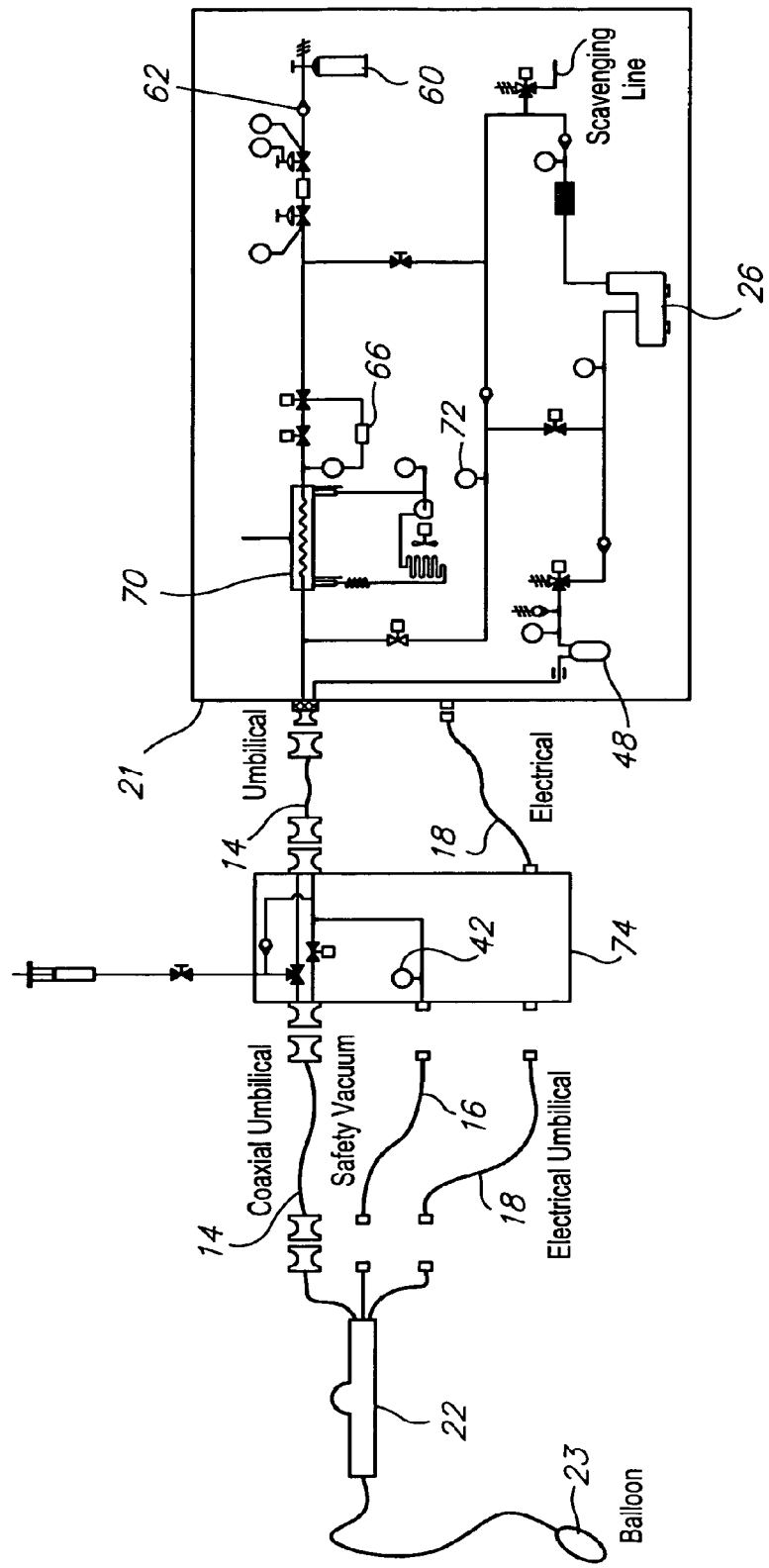
FIG. 11 is a schematic representation of the embodiment illustrated in FIG. 2E.

In FIG. 10, the refilling source 80 is located in the intermediate box 74 and inflation occurs through the outer vacuum umbilical. In FIG. 11, the refilling source is the coolant tank 60 located in the cryoablation console and inflation occurs through the inner vacuum umbilical.

Figure 12:
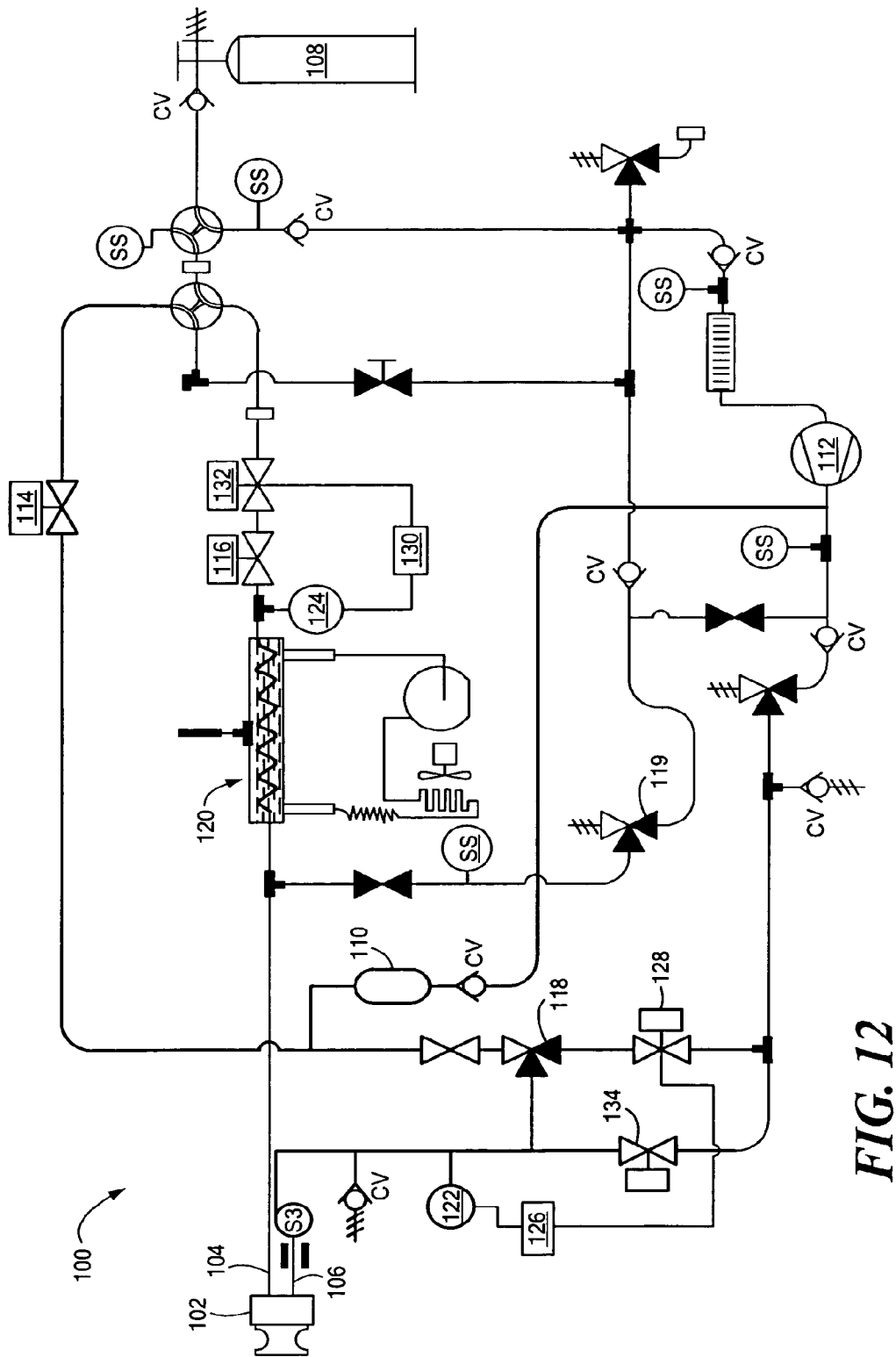
FIG. 12 is a schematic representation of an embodiment of a control console of the present invention.

Now referring to FIG. 12, a schematic representation of a console 100 for use with a medical device is shown. As previously discussed, the console 100 includes various mechanical and/or electrical components to assist in the operation, control, and/or monitoring of a medical device, such as the catheter 1 described above. Primarily, the console 100 may be coupled to the catheter 1 through an umbilical connector 102, which places a supply lumen 104 and an exhaust lumen 106 of the console 100 in fluid communication with the catheter. In general, the console 100 may further include a first coolant reservoir 108, a second coolant reservoir 110, and a vacuum source 112. As used herein, the term 'reservoir' is intended to include any container or chamber able to contain a fluid. As such, either of the first or second reservoirs may include a tank, container, or even a length of tubing or the like defining an interior space between two or more valves. The second coolant reservoir 110 may have a volumetric capacity smaller than the volumetric capacity of the first coolant reservoir 108, and the second coolant reservoir 110 may have a volumetric capacity of approximately twenty cubic centimeters, which has been shown to reduce the likelihood of cardiac abnormalities and/or failure due to coolant egress into the vascular system. The vacuum source 112 may include any structure and/or apparatus able to provide a negative pressure gradient for providing fluid flow, including pumps, plunger devices, or the like.

One or more valves may be disposed about the console 100 in fluid communication with the supply lumen 104 and/or the exhaust lumen 106 for manipulating and/or providing fluid flow along a desired path. For example, the console 100 may include a pair of valves, 114 and 116, in fluid communication with the first coolant reservoir 108 such that the first coolant reservoir 108 may be selectively switched from being in fluid communication with the second coolant reservoir 110 to being in fluid communication with the supply lumen 104. Moreover, a valve 118 may be disposed on the exhaust lumen 106 such that the exhaust lumen 106 may be selectively switched from being in fluid communication with the second coolant reservoir 110 to being in fluid communication with the vacuum source 112. In addition, the console 100 may include one or more check valves and/or pressure relief valves CV configured to open to atmosphere or to a recovery tank should a pressure level and/or flow rate within a portion of the console 100 exceed a desired or predetermined level.

The console 100 may include a valve 119 in fluid communication with both the supply lumen 104 and the exhaust lumen 106. In particular, the valve 119 may be in fluid communication with the supply lumen 104 at a position upstream of the umbilical connector 102, while being in fluid communication with the exhaust lumen 106 downstream from the umbilical connector 102. The valve 119 may further be placed in fluid communication with the surrounding atmosphere to vent excess coolant and/or to relieve or equalize pressure in both the exhaust and supply lumens. During operation, the console 100 may detect a failure of the medical device, such as an indication of the presence of blood or bodily fluid being entrained into the coolant system. Upon such detection, coolant flow may be terminated. However, despite the termination of coolant flow, due to the built-up pressure levels in the supply and exhaust lumens, bodily fluid may continue to be siphoned into the medical device and thus into portions of the console 100. To reduce the likelihood that siphoning occurs, the valve 119 may be actuated to place both the supply lumen 104 and the exhaust lumen 106 into fluid communication with the atmosphere. By doing so, the pressure in either lumen will be substantially equalized and thus will prevent the further ingress of bodily fluids into the medical device and thus the console. Of course, the equalization and/or subjection of both the supply and exhaust lumens may be achieved by using one or more valves in various configuration.

The console 100 may also include a subcooler 120 disposed about a portion of the supply lumen 104 for achieving a desired temperature and/or coolant phase of fluid flowing therethrough. The subcooler 120 may include a compressor, condenser and the like placed in thermal communication with the supply lumen 104 as previously discussed.

One or more sensors may be disposed about the supply and exhaust lumens of the console 100 for detecting temperature, pressure, and/or flow rates through a particular portion of the console 100 plumbing. For example, a first pressure sensor 122 may be disposed about the exhaust lumen 106 proximate to the umbilical connector 102. In addition, a second pressure sensor 124 may be disposed about the supply lumen 104. Of course, additional sensors SS may be included throughout the console 100 for monitoring and/or controlling particular portions of the console and properties thereof.

In addition to the one or more sensors, one or more controllers may be coupled to the sensors, and in turn, coupled to one or more of the valves situated throughout the console 100 such that the valves may be controllably manipulated in response to information obtained by the sensors. For example, a first controller 126 may be coupled to the first pressure sensor 122, wherein the first controller 126 is further coupled to a valve 128 disposed on a portion of the exhaust line, and where the valve 128 may also be in fluid communication with the vacuum source 112. In addition, a second controller 130 may be coupled to the second pressure sensor 124, where the second controller 130 is further coupled to a valve 132 disposed about the supply lumen 104. Accordingly, fluid flow through portions of the exhaust and/or supply lumens may be controllably manipulated in direct response to the information obtained by sensors contained therein.

Figure 13:
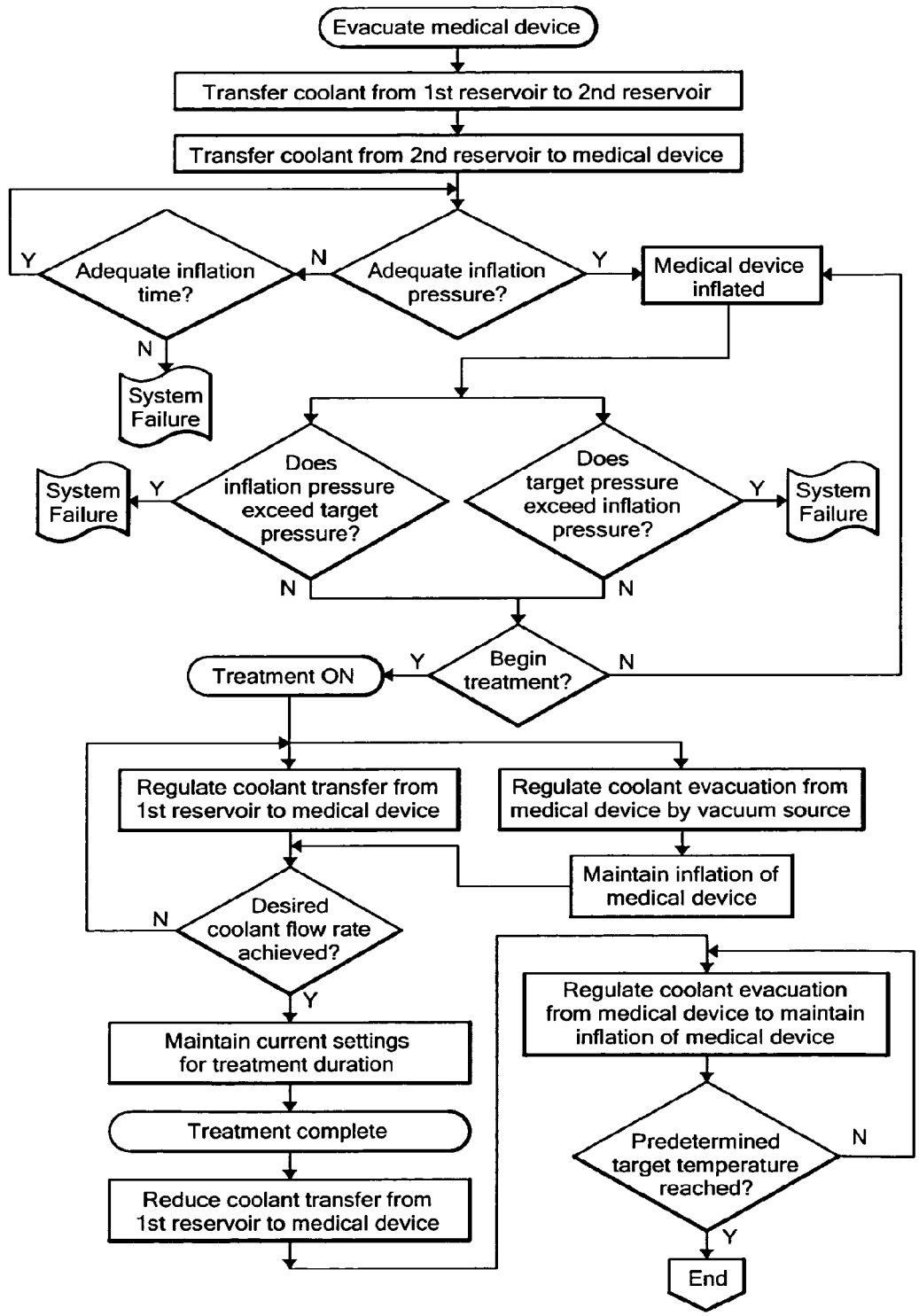
FIG. 13 is a flow chart of an exemplary use of a control console in accordance with the present invention.

In an exemplary use, the console 100 may be used for operating a medical device, such as the catheter 1, through four different phases. A flow chart of such an exemplary use is provided in FIG. 13. As previously discussed, the first phase is the evacuation or flushing phase, in which a medical device is substantially evacuated of any fluid. During this phase, a valve 134 disposed on the exhaust lumen 106 between the umbilical connector 102 and the vacuum source 112 is opened, thereby subjecting the medical device to a reduced pressure gradient and providing for the evacuation of any fluid therein. The valve 116 may be closed to prevent fluid from being drawn from the first coolant reservoir 108, and further, the valve 118 may be in a configuration such that the second coolant reservoir is also isolated from the pressure differential created by the vacuum source 112. Once evacuated to a suitable degree, the catheter may be positioned in and/or around a particular region of a patient to be treated.

During an inflation stage of use, coolant is transferred from the first coolant reservoir 108 to the second coolant reservoir 110, and subsequently to an attached medical device. The coolant flowing from the first coolant reservoir 108 to the second coolant reservoir 110 may consist of coolant vapor in a gaseous state obtained from the first coolant reservoir 108. The coolant transfer may be achieved by having the valve 116 in a closed position, while opening valve 114, thereby placing the first coolant reservoir 108 in fluid communication with the second coolant reservoir 110 rather than the supply line of the console 100. Once the second coolant reservoir 110 has been adequately filled with coolant to a desired level, the coolant from the second coolant reservoir 110 may then be transferred towards the exhaust lumen 106 of the console 100, and subsequently to the exhaust line of the coupled medical device, such as catheter 1. During the transfer from the first reservoir 108 to the second coolant reservoir 110, the valve 118 may be configured to prevent coolant from being transferred into the exhaust lumen until desired.

In the inflation phase, both the valve 116 and the valve 134 are closed, while valve 118 provides fluid communication between the second coolant reservoir 110 and the exhaust lumen 106 at the umbilical connector 102, and thus providing fluid communication with the exhaust lumen 106 of the catheter. Since both valves 116 and 134 are closed, the catheter is configured into a closed system with the coolant from the second coolant reservoir 110. Accordingly, the volume of coolant provided to the catheter from the second coolant reservoir 110 may be adjusted to provide an expected or predetermined pressure level within a portion of the medical device. In particular, as in the case with the catheter, the fixed volume being provided by the second coolant reservoir 110 may be selected to produce a target inflation pressure in the balloon of the catheter. This target level may be used to insure that the balloon is indeed inflated to a desired degree. While a particular desired or target pressure within a portion of the medical device may vary by application or specification of a particular medical device, the target pressure may be in a range of approximately atmospheric pressure to approximately 30 psia. Moreover, as the pressure within the exhaust lumen 106, and thus the balloon of the catheter, can be monitored with the pressure sensor 122, any variation in the measured pressure from the expected pressure level may indicate a leak or failure of the medical device. Moreover, as previously discussed, the second coolant reservoir 110 may have a smaller capacity than the first coolant reservoir 108, and as such, should the medical device experience a failure or leak, the amount of coolant escaping into the patient is thereby limited in amount to the capacity of the second coolant reservoir 110 rather than the first coolant reservoir 108. This limited capacity may prevent and/or reduce the likelihood of complications arising from excess coolant entering the bloodstream, as previously suggested. In addition to verifying the structural integrity of the medical device and providing a safeguard, the inflation stage allows a physician to securely position a medical device prior to actually effecting treatment of the target tissue.

Following the inflation phase is a transition phase of use for the console 100 and/or medical device. The transition phase includes providing increased coolant flow within the medical device while ensuring that the balloon does not deflate, which could cause the physician to lose the desired positioning of the medical device. In particular, the transition phase may include opening valve 116, and further switching valve 118 to place the exhaust lumen 106 in fluid communication with the controlled valve 128. As such, the balloon of the catheter 1 is placed in fluid communication with the first coolant reservoir 108 through the supply lumen 104, and is further placed in fluid communication with the vacuum source 112 through the exhaust lumen 106.

Subsequently, coolant, perhaps in a liquid state, may be transferred from the first coolant reservoir 108 through the supply lumen 104 to the balloon such that the coolant flow is regulated and/or controlled by the operation of the valve 132, which, as previously described, may be controlled by the second controller 130 in response to the second pressure sensor 124. In addition, the coolant flow through the balloon and the exhaust line may also be affected by the operation of valve 128, which may be manipulated via a feedback loop with the first controller 126 and the first pressure sensor 122.

The operation of the two controllers and the adjustable valves 132 and 128 may occur substantially simultaneously and/or alternatively in order to maintain the inflation of the balloon of the catheter at a desired and/or target pressure as coolant flow through the medical device is increased to achieve a desired or target flow rate. For example, the 132 valve may be manipulated to provide stepped increases in flow rate and/or flow pressure from the first coolant reservoir 108 to the supply lumen 104, where the 128 valve is adjusted in response to the setting of the valve 132 to provide adequate fluid communication with the vacuum source 112 to achieve the desired target coolant flow rate through the medical device.

While a suitable coolant flow rate may vary depending on the particular treatment being sought and/or depending on the dimensions and specifications of a particular medical device, the target coolant flow rate may be in the range of approximately 2500 sccm to 5000 sccm. The transition phase is ended when the target coolant flow rate is achieved and/or wherein further manipulation of the adjustable valves 132 and 128 is no longer desired. The transition phase may further be completed upon subjecting the supply lumen 104 and exhaust lumen 106 to an unimpeded, maximum flow rate providable by the first coolant reservoir 108 and the vacuum source 112.

Following the transition phase and once a desired coolant flow rate has been achieved, the console 100 may be operated in a treatment phase. The treatment phase generally includes providing coolant flow to the medical device at the target coolant flow rate such that the desired thermal treatment may be provided to the target tissue. For example, the particular treatment may include the ablation of tissue, which may be achieved by the temperature resulting in a portion of the medical device due to the coolant flow therein.

Upon completion of the treatment phase, coolant flow to the medical device may be reduced and or eliminated, but the balloon of the medical device may remain in an inflated state until a predetermined target temperature has been reached. As previously discussed, in order to avoid or reduce the likelihood of unwanted tissue damage due to cryoadhesion of the device to the tissue, it may be desired to ensure that any adhesion is eliminated prior to removal and/or repositioning of the medical device. In a particular example, coolant flow from the first coolant reservoir 108 may be reduced and/or terminated, such as by closing valve 116. In turn, valve 134 may be closed such that the adjustable valve 128 may regulate coolant evacuation from the exhaust line and thus the medical device. The valve 128 may correspondingly allow for the evacuation of coolant at a controllable rate such the balloon of the medical device remains in an inflated state until a predetermined target temperature is achieved at the balloon. While applications may vary, the target temperature may be a temperature above approximately −10° C. to 20° C. to ensure that any ice formation is thawed, and the temperature in the balloon may be monitored by one or more temperature sensors affixed to the medical device in communication with the console 100. The temperature may be monitored by a temperature sensor within the balloon, but may further be monitored by a sensor positioned on an outer surface of the balloon or by a sensor in thermal communication with a supply or exhaust lumen of the medical device. Upon achieving the predetermined target temperature, the valve 134 may then be opened, subjecting the medical device to a substantially unimpeded pressure gradient provided by the vacuum source 112, and thus allowing the balloon to collapse by the evacuation of coolant therein.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method of operating a medical device having an expandable element in fluid communication with a supply lumen and an exhaust lumen, the method comprising the steps of:
   providing a first coolant reservoir, a second coolant reservoir and a vacuum source, wherein the first coolant reservoir, the second coolant reservoir, and the vacuum source are in fluid communication with the expandable element of the medical device;
   transferring coolant from the first coolant reservoir to the second coolant reservoir;
   transferring the coolant from the second coolant reservoir to the expandable element through the exhaust lumen, wherein the expandable element is inflated to a target pressure;
   transferring the coolant from the first coolant reservoir to the expandable element through the supply lumen; and
   evacuating the coolant from the expandable element with the vacuum source,
   wherein the steps of transferring the coolant from the first coolant reservoir to the expandable element and evacuating the coolant from the expandable element are regulated to achieve a target coolant flow rate while maintaining a pressure in the expandable element at a level substantially equal to or greater than the target pressure.

2. The method according to claim 1, further comprising the steps of:
   terminating the transferring of the coolant from the first coolant reservoir to the expandable element;
   wherein the pressure is maintained in the expandable element at the level substantially equal to or greater than the target pressure until the expandable element achieves a predetermined temperature.

3. The method according to claim 1, wherein the step of transferring the coolant from the first coolant reservoir to the expandable element includes a stepped increase of coolant transfer.

4. The method according to claim 1, wherein the coolant transferred from the second coolant reservoir to the expandable element is in a gaseous state.

5. The method according to claim 4, wherein the coolant transferred from the first coolant reservoir to the expandable element is in a liquid state.

6. The method according to claim 1, wherein the target coolant flow rate is greater than approximately 2500 sccm.

7. The method according to claim 1, wherein the target pressure is greater than approximately atmospheric pressure.

8. The method according to claim 1, wherein the second coolant reservoir defines a volumetric capacity substantially less than a volumetric capacity of the first coolant reservoir.

9. The method according to claim 8, wherein the volumetric capacity of the second coolant reservoir is less than approximately twenty cubic centimeters.

10. The method according to claim 1, wherein the second coolant reservoir is defined by a length of tubing defining a lumen therein.

11. The method according to claim 1, further comprising a step of placing both the supply and the exhaust lumen in fluid communication with the atmosphere upon an indication of medical device malfunction.

* * * * *